(12) United States Patent
Qin et al.

(10) Patent No.: US 11,591,755 B2
(45) Date of Patent: Feb. 28, 2023

(54) PAPER TISSUE WITH HIGH BULK AND LOW LINT

(71) Applicant: Kimberly-Clark Worldwide, Inc., Neenah, WI (US)

(72) Inventors: Jian Qin, Appleton, WI (US); Deborah J. Calewarts, Winneconne, WI (US); Donald E. Waldroup, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 625 days.

(21) Appl. No.: 15/773,416

(22) PCT Filed: Nov. 1, 2016

(86) PCT No.: PCT/US2016/059931
§ 371 (c)(1),
(2) Date: May 3, 2018

(87) PCT Pub. No.: WO2017/079169
PCT Pub. Date: May 11, 2017

(65) Prior Publication Data
US 2018/0320318 A1 Nov. 8, 2018

Related U.S. Application Data

(60) Provisional application No. 62/250,242, filed on Nov. 3, 2015.

(51) Int. Cl.
*A61F 13/15* (2006.01)
*D21H 27/00* (2006.01)
(Continued)

(52) U.S. Cl.
CPC ..... *D21H 27/004* (2013.01); *A61F 13/15203* (2013.01); *A61F 13/53* (2013.01);
(Continued)

(58) Field of Classification Search
CPC .............. A61F 13/15203; A61F 13/534; A61F 2013/15308; A61F 2013/15357;
(Continued)

(56) References Cited

U.S. PATENT DOCUMENTS 2,105,711 A   1/1938  Weathered
2,791,523 A   5/1957  Schoen
(Continued)

FOREIGN PATENT DOCUMENTS

AT    517303 A1   12/2016
AT    519414 A2    6/2018
(Continued)

OTHER PUBLICATIONS

Copending U.S. Appl. No. 15/773,438, filed May 3, 2018, by Qin et al. for "Foamed Composite Web With Low Wet Collapse".

*Primary Examiner* — Catharine L Anderson
(74) *Attorney, Agent, or Firm* — Kimberly-Clark Worldwide, Inc.

(57) ABSTRACT

A tissue paper product is provided having at least one ultra-low density ply having a highly porous, open-celled structure and that comprises cellulosic fibers, a water insoluble binder and a foaming surfactant. The cellulosic fiber comprises greater than 50% by weight of the ply and are bonded to one another by hydrogen bonding. Further, the ply has a density less than about 0.04 g/cc and yet still provides low lint and high strength properties with the use of minimal binder. The ultra-low density ply may comprise or be included in sheets forming a stack of dispensable wipers or may be employed as or part of an absorbent core or liquid distribution layer of a personal care absorbent personal care product such as a diaper or feminine pad.

22 Claims, 2 Drawing Sheets

(51) Int. Cl.

| | | |
|---|---|---|
| *D21H 21/56* | (2006.01) | |
| *A61F 13/53* | (2006.01) | |
| *A61F 13/534* | (2006.01) | |
| *A61L 15/22* | (2006.01) | |
| *A61L 15/28* | (2006.01) | |
| *A61L 15/42* | (2006.01) | |
| *A61L 15/60* | (2006.01) | |
| *B01J 20/24* | (2006.01) | |
| *B01J 20/28* | (2006.01) | |
| *B65D 83/08* | (2006.01) | |
| *D21H 21/08* | (2006.01) | |
| *D21H 21/20* | (2006.01) | |
| *D21H 27/38* | (2006.01) | |
| *D21H 27/40* | (2006.01) | |
| *A47K 10/42* | (2006.01) | |

(52) U.S. Cl.
CPC .......... *A61F 13/534* (2013.01); *A61L 15/225* (2013.01); *A61L 15/28* (2013.01); *A61L 15/425* (2013.01); *A61L 15/60* (2013.01); *B01J 20/24* (2013.01); *B01J 20/28038* (2013.01); *B65D 83/0805* (2013.01); *D21H 21/08* (2013.01); *D21H 21/20* (2013.01); *D21H 21/56* (2013.01); *D21H 27/002* (2013.01); *D21H 27/005* (2013.01); *D21H 27/38* (2013.01); *D21H 27/40* (2013.01); *A47K 10/421* (2013.01); *A61F 2013/15357* (2013.01); *A61F 2013/15422* (2013.01); *A61F 2013/530211* (2013.01); *A61F 2013/530343* (2013.01); *A61F 2013/53472* (2013.01); *A61F 2013/530481* (2013.01); *A61F 2013/530802* (2013.01)

(58) Field of Classification Search
CPC .......... A61F 2013/15422; A61F 2013/530211; A61F 2013/5315; A61F 2013/53472; A61F 2013/5349; A47K 10/421; D21H 21/20; D21H 27/002; D21H 27/004; D21H 27/005; D21H 27/38; D21H 27/40
See application file for complete search history.

(56) References Cited

U.S. PATENT DOCUMENTS

| | | |
|---|---|---|
| 3,007,840 A | 11/1961 | Wilcox |
| 3,369,699 A | 2/1968 | Enloe |
| 3,369,700 A | 2/1968 | Nelson |
| 3,401,927 A | 9/1968 | Frick |
| 3,485,706 A | 12/1969 | Evans |
| 3,506,538 A | 4/1970 | Friedberg et al. |
| 3,542,640 A | 11/1970 | Friedberg et al. |
| 3,556,932 A | 1/1971 | Coscia |
| 3,556,933 A | 1/1971 | Coscia |
| 3,585,104 A | 6/1971 | Kleinert |
| 3,615,975 A | 10/1971 | Gillern et al. |
| 3,620,903 A | 11/1971 | Wallar, Jr. |
| 3,700,623 A | 10/1972 | Keim |
| 3,716,449 A | 2/1973 | Gatward et al. |
| 3,772,076 A | 11/1973 | Keim |
| 3,798,122 A | 3/1974 | Appel |
| 3,837,999 A | 9/1974 | Chung |
| 3,839,142 A | 10/1974 | Clarke et al. |
| 3,849,241 A | 11/1974 | Butin |
| 3,855,158 A | 12/1974 | Petrovich |
| 3,867,225 A | 2/1975 | Nystrand |
| 3,871,952 A | 3/1975 | Robertson |
| 3,899,388 A | 8/1975 | Petrovich |
| 3,929,560 A | 12/1975 | Holik et al. |
| 3,938,782 A | 2/1976 | Robertson |
| 3,966,540 A | 6/1976 | Selander et al. |
| 4,007,083 A | 2/1977 | Ring et al. |
| 4,041,203 A | 8/1977 | Brock |
| 4,049,491 A | 9/1977 | Brandon et al. |
| 4,062,721 A | 12/1977 | Guyer et al. |
| 4,100,324 A | 7/1978 | Anderson |
| 4,123,787 A | 10/1978 | Leclerc du Sablon et al. |
| 4,129,528 A | 12/1978 | Petrovich |
| 4,147,586 A | 4/1979 | Petrovich |
| 4,191,609 A | 3/1980 | Trokhan |
| 4,200,488 A | 4/1980 | Brandon et al. |
| 4,222,921 A | 9/1980 | Van Eenam |
| 4,285,767 A | 8/1981 | Page |
| 4,288,475 A | 9/1981 | Meeker |
| 4,299,655 A | 11/1981 | Skaugen |
| 4,320,162 A | 3/1982 | Schulz |
| 4,340,563 A | 7/1982 | Appel |
| 4,394,930 A | 7/1983 | Korpman |
| 4,415,388 A | 11/1983 | Korpman |
| 4,443,232 A | 4/1984 | Kaiser |
| 4,443,297 A | 4/1984 | Cheshire et al. |
| 4,443,299 A | 4/1984 | Cheshire et al. |
| 4,443,513 A | 4/1984 | Meitner |
| 4,464,224 A | 8/1984 | Matolcsy |
| 4,478,615 A | 10/1984 | Kaiser |
| 4,498,956 A | 2/1985 | Cheshire et al. |
| 4,502,675 A | 3/1985 | Clark |
| 4,543,156 A | 9/1985 | Cheshire et al. |
| 4,548,856 A | 10/1985 | Ali Khan |
| 4,559,243 A | 12/1985 | Passler et al. |
| 4,594,130 A | 6/1986 | Chang |
| 4,613,627 A | 9/1986 | Sherman et al. |
| 4,655,950 A | 4/1987 | Michalek |
| 4,686,006 A | 8/1987 | Cheshire et al. |
| 4,699,823 A | 10/1987 | Kellenberger |
| 4,734,321 A | 3/1988 | Radvan et al. |
| 4,764,253 A | 8/1988 | Cheshire et al. |
| 4,773,408 A | 9/1988 | Cilento et al. |
| 4,773,409 A | 9/1988 | Cilento et al. |
| 4,778,477 A | 10/1988 | Lauchenauer |
| 4,785,030 A | 11/1988 | Noda |
| 4,793,898 A | 12/1988 | Laamanen |
| 4,853,281 A | 8/1989 | Win |
| 4,863,064 A | 9/1989 | Dailey |
| 4,883,478 A | 11/1989 | Lerailler et al. |
| D305,181 S | 12/1989 | Veith |
| 4,894,118 A | 1/1990 | Edwards |
| 4,939,030 A | 7/1990 | Tsuji et al. |
| 4,940,513 A | 7/1990 | Spendel |
| 4,942,077 A | 7/1990 | Wendt |
| 4,944,843 A | 7/1990 | Wallace et al. |
| 4,948,007 A | 8/1990 | Berg et al. |
| 4,952,448 A | 8/1990 | Bullock et al. |
| 4,969,975 A | 11/1990 | Biggs et al. |
| 4,973,382 A | 11/1990 | Kinn et al. |
| 4,985,467 A | 1/1991 | Kelly et al. |
| 5,006,373 A | 4/1991 | Woodmansee et al. |
| 5,008,306 A | 4/1991 | Goguelin |
| 5,009,747 A | 4/1991 | Viazmensky |
| 5,013,405 A | 5/1991 | Izard |
| 5,064,653 A | 11/1991 | Sessions et al. |
| 5,065,752 A | 11/1991 | Sessions et al. |
| 5,073,416 A | 12/1991 | Avakian et al. |
| 5,098,778 A | 3/1992 | Minnick |
| 5,102,501 A | 4/1992 | Eber et al. |
| 5,134,959 A | 8/1992 | Woodmansee et al. |
| 5,137,551 A | 8/1992 | Ahrens et al. |
| 5,147,345 A | 9/1992 | Young et al. |
| 5,153,058 A | 10/1992 | Hall et al. |
| 5,164,045 A | 11/1992 | Awofeso et al. |
| 5,178,729 A | 1/1993 | Janda |
| 5,196,090 A | 3/1993 | Corbellini et al. |
| 5,200,035 A | 4/1993 | Bhat et al. |
| 5,227,023 A | 7/1993 | Pounder et al. |
| 5,238,534 A | 8/1993 | Manning et al. |
| 5,260,017 A | 11/1993 | Giles |
| 5,260,345 A | 11/1993 | DesMarais et al. |
| 5,268,224 A | 12/1993 | DesMarais et al. |
| 5,284,703 A | 2/1994 | Everhart |
| 5,300,565 A | 4/1994 | Berg et al. |

(56) References Cited

U.S. PATENT DOCUMENTS

| | | |
|---|---|---|
| 5,308,565 A | 5/1994 | Weber et al. |
| 5,310,398 A | 5/1994 | Yoneyama |
| 5,318,554 A | 6/1994 | Young et al. |
| 5,328,935 A | 7/1994 | Van Phan et al. |
| 5,330,822 A | 7/1994 | Berg et al. |
| 5,331,015 A | 7/1994 | DesMarais et al. |
| 5,338,766 A | 8/1994 | Phan et al. |
| 5,344,866 A | 9/1994 | Hall |
| 5,348,453 A | 9/1994 | Baran et al. |
| 5,350,624 A | 9/1994 | Georger |
| 5,364,382 A | 11/1994 | Latimer |
| 5,369,007 A | 11/1994 | Kidwell |
| 5,372,766 A | 12/1994 | Roe |
| 5,382,400 A | 1/1995 | Pike |
| 5,384,179 A | 1/1995 | Roe et al. |
| 5,387,207 A | 2/1995 | Dyer et al. |
| 5,393,379 A | 2/1995 | Parrinello |
| 5,397,316 A | 3/1995 | LaVon et al. |
| 5,397,626 A | 3/1995 | Berg et al. |
| 5,409,572 A | 4/1995 | Kershaw et al. |
| 5,415,640 A | 5/1995 | Kirby |
| 5,428,076 A | 6/1995 | Roe |
| 5,434,194 A | 7/1995 | Fujimoto et al. |
| 5,443,691 A | 8/1995 | Phan |
| 5,451,452 A | 9/1995 | Phan et al. |
| 5,458,592 A | 10/1995 | Abuto |
| 5,468,437 A | 11/1995 | Hall |
| 5,506,046 A | 4/1996 | Andersen et al. |
| 5,506,277 A | 4/1996 | Griesbach |
| 5,508,072 A | 4/1996 | Andersen et al. |
| 5,522,967 A | 6/1996 | Shet |
| 5,524,759 A | 6/1996 | Herzberg |
| 5,527,300 A | 6/1996 | Sauer |
| 5,533,244 A | 7/1996 | Wadzinski |
| 5,536,264 A | 7/1996 | Hsueh et al. |
| 5,545,450 A | 8/1996 | Andersen et al. |
| 5,549,589 A | 8/1996 | Horney et al. |
| 5,550,167 A | 8/1996 | DesMarais |
| 5,560,878 A | 10/1996 | Dragoo et al. |
| 5,563,179 A | 10/1996 | Stone et al. |
| D375,633 S | 11/1996 | Spanagel et al. |
| 5,571,618 A | 11/1996 | Hansen |
| 5,571,849 A | 11/1996 | DesMarais |
| 5,575,874 A | 11/1996 | Griesbach |
| 5,580,624 A | 12/1996 | Andersen et al. |
| 5,582,670 A | 12/1996 | Andersen et al. |
| 5,585,432 A | 12/1996 | Lee et al. |
| 5,586,842 A | 12/1996 | Bae et al. |
| 5,595,628 A | 1/1997 | Gordon |
| 5,599,334 A | 2/1997 | Johnston et al. |
| 5,601,542 A | 2/1997 | Melius |
| 5,612,385 A | 3/1997 | Ceaser et al. |
| D378,876 S | 4/1997 | Spanagel et al. |
| 5,618,341 A | 4/1997 | Andersen et al. |
| 5,624,971 A | 4/1997 | Wilson |
| 5,626,857 A | 5/1997 | Thimineur et al. |
| 5,631,053 A | 5/1997 | Andersen et al. |
| 5,632,737 A | 5/1997 | Stone et al. |
| 5,633,291 A | 5/1997 | Dyer et al. |
| 5,649,409 A | 7/1997 | Gujer et al. |
| 5,650,222 A | 7/1997 | DesMarais et al. |
| D381,810 S | 8/1997 | Schultz et al. |
| 5,658,603 A | 8/1997 | Andersen et al. |
| 5,660,900 A | 8/1997 | Andersen et al. |
| 5,660,903 A | 8/1997 | Andersen et al. |
| 5,660,904 A | 8/1997 | Andersen et al. |
| 5,662,731 A | 9/1997 | Andersen et al. |
| 5,665,442 A | 9/1997 | Andersen et al. |
| 5,667,635 A | 9/1997 | Win |
| 5,672,248 A | 9/1997 | Wendt |
| 5,674,917 A | 10/1997 | Wilson |
| 5,679,145 A | 10/1997 | Andersen et al. |
| 5,679,218 A | 10/1997 | Vinson et al. |
| 5,683,772 A | 11/1997 | Andersen et al. |
| 5,691,014 A | 11/1997 | Andersen et al. |
| 5,692,939 A | 12/1997 | DesMarais |
| 5,693,403 A | 12/1997 | Brown et al. |
| 5,695,607 A | 12/1997 | Oriaran et al. |
| 5,702,571 A | 12/1997 | Kamps et al. |
| 5,705,203 A | 1/1998 | Andersen et al. |
| 5,705,238 A | 1/1998 | Andersen et al. |
| 5,705,239 A | 1/1998 | Andersen et al. |
| 5,705,242 A | 1/1998 | Andersen et al. |
| 5,707,474 A | 1/1998 | Andersen et al. |
| 5,707,579 A | 1/1998 | Habelski et al. |
| 5,709,827 A | 1/1998 | Andersen et al. |
| 5,709,913 A | 1/1998 | Andersen et al. |
| D390,363 S | 2/1998 | Baum et al. |
| 5,713,881 A | 2/1998 | Rezai et al. |
| 5,716,563 A | 2/1998 | Winterowd et al. |
| 5,716,675 A | 2/1998 | Andersen et al. |
| 5,719,201 A | 2/1998 | Wilson |
| 5,720,851 A | 2/1998 | Reiner |
| 5,728,743 A | 3/1998 | Dyer et al. |
| 5,736,209 A | 4/1998 | Andersen et al. |
| 5,741,581 A | 4/1998 | DesMarais et al. |
| 5,744,506 A | 4/1998 | Goldman et al. |
| 5,744,509 A | 4/1998 | Wilson et al. |
| 5,753,308 A | 5/1998 | Andersen et al. |
| 5,753,359 A | 5/1998 | Dyer et al. |
| 5,763,499 A | 6/1998 | DesMarais |
| 5,770,634 A | 6/1998 | Dyer et al. |
| 5,776,388 A | 7/1998 | Andersen et al. |
| 5,783,126 A | 7/1998 | Andersen et al. |
| 5,785,179 A | 7/1998 | Buczwinski |
| 5,795,921 A | 8/1998 | Dyer et al. |
| 5,800,416 A | 9/1998 | Seger et al. |
| 5,800,647 A | 9/1998 | Andersen et al. |
| 5,810,961 A | 9/1998 | Andersen et al. |
| 5,817,703 A | 10/1998 | Blair et al. |
| 5,830,305 A | 11/1998 | Andersen et al. |
| 5,843,055 A | 12/1998 | Seger |
| 5,843,544 A | 12/1998 | Andersen et al. |
| 5,849,155 A | 12/1998 | Gasland |
| 5,849,805 A | 12/1998 | Dyer |
| 5,851,634 A | 12/1998 | Andersen et al. |
| 5,851,648 A | 12/1998 | Stone et al. |
| 5,853,402 A | 12/1998 | Faulks et al. |
| 5,863,958 A | 1/1999 | Dyer et al. |
| 5,868,724 A | 2/1999 | Dierckes et al. |
| 5,876,643 A | 3/1999 | Biggs et al. |
| 5,879,722 A | 3/1999 | Andersen et al. |
| 5,882,479 A | 3/1999 | Oriaran et al. |
| 5,899,893 A | 5/1999 | Dyer et al. |
| 5,900,114 A | 5/1999 | Brown et al. |
| 5,904,809 A | 5/1999 | Rokman et al. |
| 5,904,812 A | 5/1999 | Salman et al. |
| 5,908,533 A | 6/1999 | Marinack et al. |
| 5,916,503 A | 6/1999 | Rettenbacher |
| 5,916,928 A | 6/1999 | Sessions et al. |
| 5,919,411 A | 7/1999 | Rezai et al. |
| 5,922,780 A | 7/1999 | Dyer et al. |
| 5,925,299 A | 7/1999 | Dierckes et al. |
| 5,928,741 A | 7/1999 | Andersen et al. |
| 5,948,710 A | 9/1999 | Pomplun |
| 5,948,829 A | 9/1999 | Wallajapet et al. |
| 5,958,186 A | 9/1999 | Holm et al. |
| 5,976,235 A | 11/1999 | Andersen et al. |
| 5,981,044 A | 11/1999 | Phan et al. |
| 5,985,434 A | 11/1999 | Qin et al. |
| 5,994,615 A | 11/1999 | Dodge |
| 6,001,218 A | 12/1999 | Hsu et al. |
| 6,012,572 A | 1/2000 | Heathcock |
| 6,013,293 A | 1/2000 | De Moor |
| 6,013,589 A | 1/2000 | DesMarais et al. |
| 6,017,833 A | 1/2000 | Reiner et al. |
| 6,019,871 A | 2/2000 | Rokman et al. |
| 6,022,615 A | 2/2000 | Rettenbacher |
| 6,027,610 A | 2/2000 | Back et al. |
| 6,030,673 A | 2/2000 | Andersen et al. |
| 6,037,282 A | 3/2000 | Milding et al. |
| 6,043,317 A | 3/2000 | Mumick |
| D423,232 S | 4/2000 | Reid |
| 6,051,104 A | 4/2000 | Oriaran et al. |

(56) References Cited

U.S. PATENT DOCUMENTS

| | | |
|---|---|---|
| 6,054,022 A | 4/2000 | Helwig et al. |
| 6,074,527 A | 6/2000 | Hsu et al. |
| 6,075,179 A | 6/2000 | McCormack |
| 6,077,390 A | 6/2000 | Salman et al. |
| 6,077,590 A | 6/2000 | Archer et al. |
| 6,083,211 A | 7/2000 | DesMarais |
| 6,083,586 A | 7/2000 | Andersen et al. |
| 6,086,718 A | 7/2000 | Carter et al. |
| 6,090,195 A | 7/2000 | Andersen et al. |
| 6,093,359 A | 7/2000 | Gauchel et al. |
| 6,096,809 A | 8/2000 | Lorcks et al. |
| 6,103,060 A | 8/2000 | Munerelle et al. |
| 6,103,063 A | 8/2000 | Oriaran et al. |
| 6,111,163 A | 8/2000 | McCormack |
| D430,406 S | 9/2000 | Ingalls |
| D430,407 S | 9/2000 | Ingalls |
| D430,734 S | 9/2000 | Bredendick et al. |
| 6,113,740 A | 9/2000 | Oriaran et al. |
| D431,371 S | 10/2000 | Ingalls et al. |
| D431,372 S | 10/2000 | Ingalls et al. |
| 6,129,720 A | 10/2000 | Blenke |
| 6,133,193 A | 10/2000 | Kajikawa et al. |
| 6,136,153 A | 10/2000 | Rokman et al. |
| 6,136,873 A | 10/2000 | Hahnle et al. |
| 6,153,053 A | 11/2000 | Harper et al. |
| 6,160,028 A | 12/2000 | Dyer |
| 6,162,961 A | 12/2000 | Tanner et al. |
| 6,163,943 A | 12/2000 | Johansson et al. |
| D436,738 S | 1/2001 | Bredendick et al. |
| 6,168,857 B1 | 1/2001 | Andersen et al. |
| 6,174,152 B1 | 1/2001 | Rokman et al. |
| 6,174,929 B1 | 1/2001 | Hähnle et al. |
| D437,119 S | 2/2001 | Jahner et al. |
| D437,120 S | 2/2001 | Jahner et al. |
| D437,489 S | 2/2001 | Jahner et al. |
| D438,017 S | 2/2001 | Reid |
| 6,193,838 B1 | 2/2001 | Oriaran et al. |
| 6,200,404 B1 | 3/2001 | Andersen et al. |
| 6,200,669 B1 | 3/2001 | Marmon |
| 6,203,663 B1 | 3/2001 | Kamps et al. |
| 6,207,244 B1 | 3/2001 | Hesch |
| D440,051 S | 4/2001 | Bredendick et al. |
| 6,214,907 B1 | 4/2001 | Tomka |
| 6,224,714 B1 | 5/2001 | Schroeder |
| 6,224,977 B1 | 5/2001 | Kobylivker |
| 6,231,960 B1 | 5/2001 | Dyer et al. |
| 6,231,970 B1 | 5/2001 | Andersen et al. |
| 6,235,816 B1 | 5/2001 | Lorcks et al. |
| 6,238,518 B1 | 5/2001 | Rokman et al. |
| D443,766 S | 6/2001 | Bredendick et al. |
| 6,243,934 B1 | 6/2001 | Wadzinski |
| 6,245,410 B1 | 6/2001 | Hähnle et al. |
| 6,245,697 B1 | 6/2001 | Conrad et al. |
| 6,248,211 B1 | 6/2001 | Jennings et al. |
| 6,251,207 B1 | 6/2001 | Schultz et al. |
| 6,258,203 B1 | 7/2001 | Rokman et al. |
| 6,261,679 B1 | 7/2001 | Chen et al. |
| 6,274,077 B1 | 8/2001 | Hur et al. |
| 6,274,667 B1 | 8/2001 | Shannon |
| 6,280,570 B1 | 8/2001 | Harper et al. |
| 6,287,417 B1 | 9/2001 | Bhat |
| 6,287,418 B1 | 9/2001 | Schroeder |
| 6,287,422 B1 | 9/2001 | Harper et al. |
| 6,296,736 B1 | 10/2001 | Hsu et al. |
| 6,296,929 B1 | 10/2001 | Gentile et al. |
| 6,309,661 B1 | 10/2001 | Haynes et al. |
| 6,346,557 B1 | 2/2002 | Argy |
| 6,355,142 B1 | 3/2002 | Ahrens |
| 6,365,667 B1 | 4/2002 | Shannon |
| 6,372,087 B2 | 4/2002 | Harper et al. |
| 6,376,032 B1 | 4/2002 | Clarke et al. |
| 6,383,960 B1 | 5/2002 | Everett |
| 6,387,210 B1 | 5/2002 | Hsu et al. |
| 6,410,823 B1 | 6/2002 | Daley |
| D459,897 S | 7/2002 | Bredendick et al. |
| 6,413,368 B1 | 7/2002 | Dwiggins et al. |
| 6,419,790 B1 | 7/2002 | Leege et al. |
| 6,425,983 B1 | 7/2002 | Marinack et al. |
| 6,432,272 B1 | 8/2002 | Hollenberg et al. |
| 6,436,234 B1 | 8/2002 | Chen et al. |
| 6,437,214 B1 | 8/2002 | Everett |
| 6,440,266 B1 | 8/2002 | George et al. |
| 6,443,258 B1 | 9/2002 | Putt et al. |
| 6,444,088 B2 | 9/2002 | Rökman et al. |
| 6,447,640 B1 | 9/2002 | Watson et al. |
| 6,451,166 B1 | 9/2002 | Marinack et al. |
| 6,454,904 B1 | 9/2002 | Hermans |
| 6,455,600 B1 | 9/2002 | Hähnle et al. |
| 6,462,159 B1 | 10/2002 | Hamada |
| 6,472,497 B2 | 10/2002 | Loercks et al. |
| 6,500,302 B2 | 12/2002 | Dwiggins et al. |
| 6,503,372 B1 | 1/2003 | Rokman et al. |
| 6,518,479 B1 | 2/2003 | Graef et al. |
| 6,525,240 B1 | 2/2003 | Graef et al. |
| 6,527,913 B1 | 3/2003 | Johnson et al. |
| 6,531,078 B2 | 3/2003 | Laine et al. |
| 6,534,149 B1 | 3/2003 | Daley |
| 6,540,879 B2 | 4/2003 | Marinack et al. |
| 6,544,386 B1 | 4/2003 | Krzysik et al. |
| 6,548,132 B1 | 4/2003 | Clarke et al. |
| 6,550,634 B1 | 4/2003 | Alegre De Miquel |
| 6,562,193 B1 | 5/2003 | Elonen et al. |
| 6,589,634 B2 | 7/2003 | Schultz et al. |
| 6,596,389 B1 | 7/2003 | Hallett et al. |
| 6,600,086 B1 | 7/2003 | Mace et al. |
| 6,603,054 B2 * | 8/2003 | Chen .................. D04H 1/68 604/369 |
| 6,612,462 B2 | 9/2003 | Sosalla |
| 6,613,424 B1 | 9/2003 | Putt et al. |
| 6,616,802 B1 | 9/2003 | Kinsley, Jr. et al. |
| 6,617,490 B1 | 9/2003 | Chen |
| 6,630,054 B1 | 10/2003 | Graef et al. |
| 6,649,025 B2 | 11/2003 | Mills et al. |
| 6,657,101 B1 | 12/2003 | Malmgren et al. |
| 6,663,611 B2 | 12/2003 | Blaney et al. |
| 6,670,522 B1 | 12/2003 | Graef et al. |
| 6,673,980 B1 | 1/2004 | Varona et al. |
| 6,673,983 B1 | 1/2004 | Graef et al. |
| 6,682,215 B2 | 1/2004 | Kinsley, Jr. et al. |
| 6,689,934 B2 | 2/2004 | Dodge, II et al. |
| 6,703,330 B1 | 3/2004 | Marsh |
| 6,706,944 B2 | 3/2004 | Qin et al. |
| 6,709,548 B2 | 3/2004 | Marinack et al. |
| 6,709,550 B2 | 3/2004 | Holz et al. |
| 6,733,631 B2 | 5/2004 | Elonen et al. |
| 6,734,335 B1 | 5/2004 | Graef et al. |
| 6,746,570 B2 | 6/2004 | Burazin et al. |
| 6,749,719 B2 | 6/2004 | Burazin et al. |
| 6,750,262 B1 | 6/2004 | Hahnle et al. |
| 6,752,905 B2 | 6/2004 | Hu |
| 6,752,907 B2 | 6/2004 | Edwards et al. |
| 6,780,356 B1 | 8/2004 | Putt et al. |
| 6,787,000 B2 | 9/2004 | Burazin et al. |
| 6,790,314 B2 | 9/2004 | Burazin et al. |
| 6,797,114 B2 | 9/2004 | Hu |
| 6,808,595 B1 * | 10/2004 | Burns .................. D21H 27/38 162/129 |
| 6,808,790 B2 | 10/2004 | Chen et al. |
| 6,811,638 B2 | 11/2004 | Close |
| 6,821,385 B2 | 11/2004 | Burazin et al. |
| 6,821,387 B2 | 11/2004 | Hu |
| 6,821,388 B2 | 11/2004 | Marsh |
| 6,824,650 B2 | 11/2004 | Lindsay et al. |
| 6,830,656 B2 | 12/2004 | Kinsley, Jr. |
| 6,837,956 B2 | 1/2005 | Cowell et al. |
| 6,837,972 B2 | 1/2005 | Marsh |
| 6,861,477 B2 | 3/2005 | Wang et al. |
| 6,867,346 B1 | 3/2005 | Dopps et al. |
| 6,875,315 B2 | 4/2005 | Bakken et al. |
| 6,878,238 B2 | 4/2005 | Bakken et al. |
| 6,887,348 B2 | 5/2005 | Hermans et al. |
| 6,893,535 B2 | 5/2005 | Hermans et al. |
| 6,921,459 B2 | 7/2005 | Kinsley, Jr. et al. |
| 6,939,914 B2 | 9/2005 | Qin et al. |

(56) References Cited

U.S. PATENT DOCUMENTS

| | | |
|---|---|---|
| 6,946,058 B2 | 9/2005 | Hu |
| 6,946,413 B2 | 9/2005 | Lange |
| 6,951,598 B2 | 10/2005 | Flugge et al. |
| 6,956,009 B2 | 10/2005 | Wang et al. |
| 6,962,645 B2 | 11/2005 | Graef et al. |
| 6,964,725 B2 | 11/2005 | Shannon et al. |
| 6,969,781 B2 | 11/2005 | Graef et al. |
| 6,983,821 B2 | 1/2006 | Putt et al. |
| D517,816 S | 3/2006 | Dwiggins et al. |
| 7,028,840 B2 | 4/2006 | Huang |
| D519,739 S | 5/2006 | Schuh et al. |
| 7,041,196 B2 | 5/2006 | Lorenz et al. |
| 7,045,026 B2 | 5/2006 | Lorenz et al. |
| 7,052,580 B2 | 5/2006 | Trokhan et al. |
| 7,066,006 B2 | 6/2006 | Minerath, III et al. |
| 7,067,038 B2 | 6/2006 | Trokhan et al. |
| 7,081,559 B2 | 7/2006 | Fujikawa et al. |
| 7,125,470 B2 | 10/2006 | Graef et al. |
| 7,141,142 B2 | 11/2006 | Burazin et al. |
| 7,155,991 B2 | 1/2007 | Minerath, III et al. |
| 7,156,954 B2 | 1/2007 | Farrington, Jr et al. |
| 7,160,418 B2 | 1/2007 | Edwards et al. |
| 7,166,190 B2 | 1/2007 | Graef et al. |
| 7,169,451 B2 | 1/2007 | Clarke et al. |
| 7,214,293 B2 | 5/2007 | Trokhan et al. |
| 7,220,821 B2 | 5/2007 | Hähnle et al. |
| 7,229,528 B2 | 6/2007 | Vinson et al. |
| 7,235,708 B2 | 6/2007 | Guidotti et al. |
| D551,406 S | 9/2007 | Caruso et al. |
| 7,285,183 B2 | 10/2007 | Kajander et al. |
| 7,287,650 B2 | 10/2007 | Koslow |
| 7,291,382 B2 | 11/2007 | Krueger et al. |
| 7,294,238 B2 | 11/2007 | Bakken et al. |
| 7,300,547 B2 | 11/2007 | Luu et al. |
| 7,311,800 B2 | 12/2007 | Russell et al. |
| 7,314,663 B2 | 1/2008 | Stelljes, Jr. et al. |
| 7,314,664 B2 | 1/2008 | Stelljes, Jr. et al. |
| 7,314,665 B2 | 1/2008 | Stelljes, Jr. et al. |
| 7,322,970 B2 | 1/2008 | Schmidt et al. |
| 7,354,502 B2 | 4/2008 | Polat et al. |
| 7,364,015 B2 | 4/2008 | Englert et al. |
| 7,374,638 B2 | 5/2008 | Horenziak et al. |
| 7,390,378 B2 | 6/2008 | Carels et al. |
| 7,396,436 B2 | 7/2008 | Trokhan et al. |
| 7,396,584 B2 | 7/2008 | Azad |
| 7,407,560 B2 | 8/2008 | Hilbig et al. |
| 7,413,629 B2 | 8/2008 | Fisher et al. |
| 7,416,636 B2 | 8/2008 | Blomqvist |
| 7,416,637 B2 | 8/2008 | Murray et al. |
| 7,435,266 B2 | 10/2008 | Sun et al. |
| 7,435,313 B2 | 10/2008 | Boatman et al. |
| 7,435,316 B2 | 10/2008 | Boatman et al. |
| 7,462,754 B2 | 12/2008 | Malowaniec |
| 7,494,563 B2 | 2/2009 | Edwards et al. |
| 7,497,923 B2 | 3/2009 | Ward et al. |
| 7,497,925 B2 | 3/2009 | Hermans et al. |
| 7,497,926 B2 | 3/2009 | Hermans et al. |
| 7,503,998 B2 | 3/2009 | Murray et al. |
| 7,524,399 B2 | 4/2009 | Hermans et al. |
| 7,524,404 B2 | 4/2009 | Boatman et al. |
| 7,527,152 B2 | 5/2009 | Lentner |
| 7,543,423 B2 | 6/2009 | Long |
| 7,585,388 B2 | 9/2009 | Yeh et al. |
| 7,585,389 B2 | 9/2009 | Yeh et al. |
| 7,597,777 B2 | 10/2009 | Wilke, II |
| 7,601,374 B2 | 10/2009 | Clarke |
| 7,629,043 B2 | 12/2009 | Lindsay et al. |
| 7,645,359 B2 | 1/2010 | Lorenz et al. |
| 7,662,257 B2 | 2/2010 | Edwards et al. |
| 7,670,457 B2 | 3/2010 | Murray et al. |
| 7,678,229 B2 | 3/2010 | Wilke, II |
| 7,682,697 B2 | 3/2010 | Raghavendran et al. |
| 7,691,228 B2 | 4/2010 | Edwards et al. |
| 7,699,959 B2 | 4/2010 | Ward et al. |
| 7,744,576 B2 | 6/2010 | Busam et al. |
| 7,750,203 B2 | 7/2010 | Becker et al. |
| 7,775,958 B2 | 8/2010 | Mukai et al. |
| 7,785,696 B2 | 8/2010 | Boatman et al. |
| 7,794,565 B2 | 9/2010 | Shannon et al. |
| 7,799,161 B2 | 9/2010 | Schuh et al. |
| 7,799,968 B2 | 9/2010 | Chen et al. |
| 7,820,008 B2 | 10/2010 | Edwards et al. |
| 7,828,932 B2 | 11/2010 | Hermans et al. |
| 7,846,296 B2 | 12/2010 | Luu et al. |
| 7,850,823 B2 | 12/2010 | Chou et al. |
| 7,851,057 B2 | 12/2010 | Englert et al. |
| 7,851,667 B2 | 12/2010 | Becker et al. |
| 7,857,941 B2 | 12/2010 | Ruthven et al. |
| 7,862,686 B2 | 1/2011 | Ward et al. |
| 7,887,676 B2 | 2/2011 | Boatman et al. |
| 7,918,951 B2 | 4/2011 | Lorenz et al. |
| 7,918,964 B2 | 4/2011 | Edwards et al. |
| 7,918,972 B2 | 4/2011 | Boatman et al. |
| 7,927,456 B2 | 4/2011 | Murray et al. |
| 7,935,860 B2 | 5/2011 | Dodge, II |
| 7,938,813 B2 | 5/2011 | Wang |
| 7,972,476 B2 | 7/2011 | Scherb et al. |
| 7,994,079 B2 | 8/2011 | Chen et al. |
| 8,007,640 B2 | 8/2011 | Boatman et al. |
| 8,017,827 B2 | 9/2011 | Hundorf et al. |
| 8,029,646 B2 | 10/2011 | Moncla |
| 8,056,733 B2 | 11/2011 | Koslow |
| 8,083,893 B2 | 12/2011 | Boatman et al. |
| 8,092,848 B2 | 1/2012 | Clarke |
| 8,102,275 B2 | 1/2012 | McGuire et al. |
| 8,110,232 B2 | 2/2012 | Clarke |
| 8,123,905 B2 | 2/2012 | Luu et al. |
| 8,142,612 B2 | 3/2012 | Murray et al. |
| 8,142,617 B2 | 3/2012 | Ruthven et al. |
| 8,143,472 B1 | 3/2012 | Bragd et al. |
| 8,152,957 B2 | 4/2012 | Edwards et al. |
| 8,152,958 B2 | 4/2012 | Super et al. |
| 8,158,689 B2 | 4/2012 | Baker et al. |
| 8,178,025 B2 | 5/2012 | Awofeso et al. |
| 8,187,240 B2 | 5/2012 | Busam et al. |
| 8,187,427 B2 | 5/2012 | Schuh et al. |
| 8,211,078 B2 | 7/2012 | Noel |
| 8,226,797 B2 | 7/2012 | Murray et al. |
| 8,257,552 B2 | 9/2012 | Edwards et al. |
| 8,293,072 B2 | 10/2012 | Super et al. |
| 8,319,005 B2 | 11/2012 | Becker et al. |
| 8,324,446 B2 | 12/2012 | Wang et al. |
| 8,328,985 B2 | 12/2012 | Edwards et al. |
| 8,361,278 B2 | 1/2013 | Fike et al. |
| 8,378,000 B2 | 2/2013 | Hintz et al. |
| 8,388,803 B2 | 3/2013 | Super et al. |
| 8,388,804 B2 | 3/2013 | Super et al. |
| 8,394,236 B2 | 3/2013 | Edwards et al. |
| 8,398,818 B2 | 3/2013 | Edwards et al. |
| 8,398,820 B2 | 3/2013 | Edwards et al. |
| 8,425,721 B2 | 4/2013 | Tynkkynen et al. |
| 8,435,381 B2 | 5/2013 | Murray et al. |
| 8,461,412 B2 | 6/2013 | Febo et al. |
| 8,496,637 B2 | 7/2013 | Hundorf et al. |
| 8,512,516 B2 | 8/2013 | Murray et al. |
| 8,524,040 B2 | 9/2013 | Edwards et al. |
| 8,540,846 B2 | 9/2013 | Miller et al. |
| 8,545,676 B2 | 10/2013 | Super et al. |
| 8,552,252 B2 | 10/2013 | Hundorf et al. |
| 8,562,786 B2 | 10/2013 | Murray et al. |
| 8,568,559 B2 | 10/2013 | Murray et al. |
| 8,568,560 B2 | 10/2013 | Murray et al. |
| 8,603,296 B2 | 12/2013 | Edwards et al. |
| 8,632,658 B2 | 1/2014 | Miller et al. |
| 8,636,874 B2 | 1/2014 | Super et al. |
| 8,647,105 B2 | 2/2014 | Awofeso et al. |
| 8,652,300 B2 | 2/2014 | Super et al. |
| 8,662,344 B2 | 3/2014 | Gispert |
| 8,673,115 B2 | 3/2014 | Edwards et al. |
| 8,674,170 B2 | 3/2014 | Busam et al. |
| 8,702,668 B2 | 4/2014 | Noel |
| 8,741,105 B2 | 6/2014 | Beaupre et al. |
| 8,766,031 B2 | 7/2014 | Becker et al. |
| 8,778,138 B2 | 7/2014 | Super et al. |

(56) References Cited

U.S. PATENT DOCUMENTS

| | | |
|---|---|---|
| 8,791,318 B2 | 7/2014 | Becker et al. |
| 8,815,056 B2 | 8/2014 | Araki et al. |
| 8,829,263 B2 | 9/2014 | Haggstrom et al. |
| 8,841,506 B2 | 9/2014 | Febo et al. |
| 8,852,397 B2 | 10/2014 | Super et al. |
| 8,864,944 B2 | 10/2014 | Miller et al. |
| 8,864,945 B2 | 10/2014 | Miller et al. |
| 8,911,592 B2 | 12/2014 | Edwards et al. |
| 8,968,516 B2 | 3/2015 | Super et al. |
| 8,979,815 B2 | 3/2015 | Roe et al. |
| 8,980,052 B2 | 3/2015 | Super et al. |
| 9,017,517 B2 | 4/2015 | Super et al. |
| 9,044,359 B2 | 6/2015 | Wciorka et al. |
| 9,051,691 B2 | 6/2015 | Miller et al. |
| 9,057,158 B2 | 6/2015 | Miller et al. |
| 9,138,360 B1 | 9/2015 | Febo et al. |
| 9,144,524 B2 | 9/2015 | Febo et al. |
| 9,216,116 B2 | 12/2015 | Roe et al. |
| 9,216,118 B2 | 12/2015 | Roe et al. |
| 9,228,048 B2 | 1/2016 | Wibaux et al. |
| 9,241,845 B2 | 1/2016 | Hundorf et al. |
| 9,243,367 B2 | 1/2016 | Rekoske et al. |
| 9,267,240 B2 | 2/2016 | Lee et al. |
| 9,279,219 B2 | 3/2016 | Edwards et al. |
| 9,309,627 B2 | 4/2016 | Miller et al. |
| 9,326,896 B2 | 5/2016 | Schäfer et al. |
| 9,333,120 B2 | 5/2016 | Lavon et al. |
| 9,334,610 B2 | 5/2016 | Kinnunen et al. |
| 9,340,363 B2 | 5/2016 | Jackels et al. |
| 9,365,977 B2 | 6/2016 | Beaupre et al. |
| 9,371,614 B2 | 6/2016 | Schuh et al. |
| 9,371,615 B2 | 6/2016 | Super et al. |
| 9,375,358 B2 | 6/2016 | Ehrnsperger et al. |
| 9,382,665 B2 | 7/2016 | Miller et al. |
| 9,388,534 B2 | 7/2016 | Super et al. |
| 9,447,543 B2 | 9/2016 | Matula |
| 9,468,566 B2 | 10/2016 | Rosati et al. |
| 9,476,162 B2 | 10/2016 | Lee et al. |
| 9,492,328 B2 | 11/2016 | Jackels et al. |
| 9,493,911 B2 | 11/2016 | Miller et al. |
| 9,532,910 B2 | 1/2017 | Rosati et al. |
| 9,572,728 B2 | 2/2017 | Ashton et al. |
| 9,579,238 B2 | 2/2017 | Noel |
| 9,603,755 B2 | 3/2017 | Tanaka |
| 9,649,232 B2 | 5/2017 | Hippe et al. |
| 9,649,830 B2 | 5/2017 | Rasch |
| 9,657,443 B2 | 5/2017 | Rekoske et al. |
| 9,662,246 B2 | 5/2017 | Collinson et al. |
| 9,668,926 B2 | 6/2017 | Jackels et al. |
| 9,708,774 B2 | 7/2017 | Lee et al. |
| 9,713,556 B2 | 7/2017 | Arizti et al. |
| 9,713,557 B2 | 7/2017 | Arizti et al. |
| 9,739,015 B2 | 8/2017 | Miller et al. |
| 9,744,755 B2 | 8/2017 | Thompson, Jr. et al. |
| 9,752,280 B2 | 9/2017 | Matula |
| 9,763,835 B2 | 9/2017 | Becker et al. |
| 9,789,009 B2 | 10/2017 | Joseph |
| 9,789,011 B2 | 10/2017 | Roe et al. |
| 9,808,554 B2 | 11/2017 | Swaniker |
| 9,822,487 B2 | 11/2017 | Ahoniemi et al. |
| 9,877,872 B2 | 1/2018 | Mumby et al. |
| 9,879,382 B2 | 1/2018 | Miller et al. |
| 9,950,309 B2 | 4/2018 | Lee et al. |
| 9,963,568 B2 | 5/2018 | Nakatsuji et al. |
| 9,974,697 B2 | 5/2018 | Lavon et al. |
| 9,974,699 B2 | 5/2018 | Kreuzer et al. |
| 9,987,176 B2 | 6/2018 | Roe et al. |
| 9,988,763 B2 | 6/2018 | Ramaratnam et al. |
| 9,994,712 B2 | 6/2018 | Cai et al. |
| 9,995,005 B2 | 6/2018 | Ramaratnam et al. |
| 10,004,647 B2 | 6/2018 | Jackels et al. |
| 10,022,280 B2 | 7/2018 | Ehrnsperger et al. |
| 10,034,800 B2 | 7/2018 | Febo et al. |
| 10,039,673 B2 | 8/2018 | Mumby et al. |
| 10,039,676 B2 | 8/2018 | LaVon |
| 10,052,242 B2 | 8/2018 | Bianchi et al. |
| 10,065,175 B2 | 9/2018 | Lee et al. |
| 10,071,002 B2 | 9/2018 | Bianchi et al. |
| 10,076,449 B2 | 9/2018 | Allen et al. |
| 10,099,425 B2 | 10/2018 | Miller, IV et al. |
| 10,130,519 B2 | 11/2018 | Mumby et al. |
| 10,130,525 B2 | 11/2018 | Rosati et al. |
| 10,130,527 B2 | 11/2018 | Peri et al. |
| 10,137,039 B2 | 11/2018 | Stelzig et al. |
| 10,138,600 B2 | 11/2018 | Jannari et al. |
| 10,149,788 B2 | 12/2018 | Kreuzer et al. |
| 10,190,263 B2 | 1/2019 | Ramaratnam et al. |
| 10,196,780 B2 | 2/2019 | Lee et al. |
| 10,201,644 B2 | 2/2019 | Haggstrom et al. |
| 10,208,426 B2 | 2/2019 | Sealey et al. |
| 10,221,350 B2 | 3/2019 | Shalagina et al. |
| 10,231,874 B2 | 3/2019 | Mumby et al. |
| 10,245,188 B2 | 4/2019 | Jackels et al. |
| 10,247,195 B2 | 4/2019 | Manninen et al. |
| 10,259,151 B2 | 4/2019 | Kiiskinen et al. |
| 10,273,635 B2 | 4/2019 | Miller, IV et al. |
| 10,292,875 B2 | 5/2019 | Tapp et al. |
| 10,301,775 B2 | 5/2019 | Nordström et al. |
| 10,301,779 B2 | 5/2019 | Sealey, II et al. |
| 10,322,040 B2 | 6/2019 | Stiehl et al. |
| 10,335,324 B2 | 7/2019 | Roe et al. |
| 10,619,303 B2 | 4/2020 | Thole et al. |
| 11,015,292 B2 | 5/2021 | Venema et al. |
| 11,136,700 B2 | 10/2021 | Venema et al. |
| 2001/0013389 A1 | 8/2001 | Fingal et al. |
| 2002/0007169 A1 | 1/2002 | Graef et al. |
| 2002/0013560 A1 | 1/2002 | Erspamer et al. |
| 2002/0055310 A1 | 5/2002 | Falk et al. |
| 2002/0088581 A1 | 7/2002 | Graef et al. |
| 2002/0092634 A1 | 7/2002 | Rokman et al. |
| 2002/0132121 A1 | 9/2002 | Palacio et al. |
| 2002/0183703 A1 | 12/2002 | Singh |
| 2003/0018311 A1 | 1/2003 | Graef |
| 2003/0106656 A1 | 6/2003 | Johnson et al. |
| 2003/0139715 A1 | 7/2003 | Dodge et al. |
| 2003/0167045 A1 | 9/2003 | Graef et al. |
| 2003/0171727 A1 | 9/2003 | Graef et al. |
| 2003/0220039 A1 | 11/2003 | Chen et al. |
| 2004/0045685 A1 | 3/2004 | Horner et al. |
| 2004/0063367 A1 | 4/2004 | Dodge et al. |
| 2004/0065420 A1 | 4/2004 | Graef et al. |
| 2004/0084162 A1 | 5/2004 | Shannon et al. |
| 2004/0084164 A1 | 5/2004 | Shannon et al. |
| 2004/0096642 A1 | 5/2004 | Maruyama et al. |
| 2004/0110017 A1 | 6/2004 | Lonsky et al. |
| 2004/0111817 A1 | 6/2004 | Chen et al. |
| 2004/0112783 A1 | 6/2004 | Mukai et al. |
| 2004/0115419 A1 | 6/2004 | Qin et al. |
| 2004/0115451 A1 | 6/2004 | Lonsky et al. |
| 2004/0121680 A1 | 6/2004 | Yahiaoui et al. |
| 2004/0127873 A1 | 7/2004 | Varona et al. |
| 2004/0142620 A1 | 7/2004 | Kinsley |
| 2004/0157524 A1 | 8/2004 | Polat et al. |
| 2004/0192136 A1 | 9/2004 | Gusky |
| 2004/0254551 A1 | 12/2004 | Carnes et al. |
| 2004/0256066 A1 | 12/2004 | Lindsay et al. |
| 2005/0034826 A1 | 2/2005 | Hu |
| 2005/0060933 A1 | 3/2005 | Henson |
| 2005/0090789 A1 | 4/2005 | Graef et al. |
| 2005/0095980 A1 | 5/2005 | Chang |
| 2005/0124709 A1 | 6/2005 | Krueger et al. |
| 2005/0136772 A1 | 6/2005 | Chen et al. |
| 2005/0142348 A1 | 6/2005 | Kajander et al. |
| 2005/0152954 A1 | 7/2005 | Farrell et al. |
| 2005/0211718 A1 | 9/2005 | Decker |
| 2005/0230069 A1 | 10/2005 | Hilbig et al. |
| 2005/0244627 A1 | 11/2005 | Travelute et al. |
| 2005/0245393 A1 | 11/2005 | Herfert |
| 2005/0247397 A1 | 11/2005 | Kraus et al. |
| 2005/0247416 A1 | 11/2005 | Forry et al. |
| 2005/0267226 A1 | 12/2005 | Wehr et al. |
| 2006/0005916 A1 | 1/2006 | Stelljes et al. |
| 2006/0008621 A1 | 1/2006 | Gusky |
| 2006/0011315 A1 | 1/2006 | Kinsley et al. |

(56) References Cited

U.S. PATENT DOCUMENTS

| | | |
|---|---|---|
| 2006/0030632 A1 | 2/2006 | Krueger et al. |
| 2006/0081348 A1 | 4/2006 | Graef et al. |
| 2006/0135026 A1 | 6/2006 | Arendt et al. |
| 2006/0142719 A1 | 6/2006 | Vogt et al. |
| 2006/0191357 A1 | 8/2006 | Minerath et al. |
| 2006/0246272 A1 | 11/2006 | Zhang et al. |
| 2006/0266485 A1 | 11/2006 | Knox et al. |
| 2006/0266487 A1 | 11/2006 | Scherb et al. |
| 2007/0148433 A1 | 6/2007 | Mallory et al. |
| 2007/0179210 A1 | 8/2007 | Swaniker |
| 2007/0218485 A1 | 9/2007 | Davis et al. |
| 2007/0235466 A1 | 10/2007 | Fulscher |
| 2007/0269644 A1 | 11/2007 | Harper et al. |
| 2008/0052859 A1 | 3/2008 | Orlandi |
| 2008/0121461 A1 | 5/2008 | Gross et al. |
| 2008/0179775 A1 | 7/2008 | Palm et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312625 A1 | 12/2008 | Hundorf et al. |
| 2008/0312628 A1 | 12/2008 | Hundorf et al. |
| 2009/0000753 A1 | 1/2009 | Vestola et al. |
| 2009/0001635 A1 | 1/2009 | Newson et al. |
| 2009/0008275 A1 | 1/2009 | Ferrari et al. |
| 2009/0117365 A1 | 5/2009 | Mallory et al. |
| 2009/0131898 A1 | 5/2009 | Malmgren et al. |
| 2009/0205794 A1 | 8/2009 | Scherb et al. |
| 2009/0270005 A1 | 10/2009 | Takahashi et al. |
| 2010/0075858 A1 | 3/2010 | Davis et al. |
| 2010/0132144 A1 | 6/2010 | Rautray |
| 2010/0136294 A1 | 6/2010 | Manifold et al. |
| 2010/0155284 A1 | 6/2010 | Gerstle |
| 2010/0251611 A1 | 10/2010 | Henson |
| 2010/0273716 A1 | 10/2010 | Harris |
| 2010/0327484 A1 | 12/2010 | Schuh et al. |
| 2011/0151596 A1 | 6/2011 | Cho |
| 2011/0290437 A1 | 12/2011 | Vogel |
| 2012/0121674 A1 | 5/2012 | Pedoja |
| 2014/0001196 A1* | 1/2014 | Bushman ............... B65D 83/08 221/45 |
| 2014/0009606 A1 | 1/2014 | Puccio |
| 2014/0102650 A1 | 4/2014 | Qin et al. |
| 2014/0121623 A1 | 5/2014 | Kirby |
| 2014/0158626 A1 | 6/2014 | Ziemer et al. |
| 2014/0189970 A1 | 7/2014 | Fingal et al. |
| 2014/0231037 A1 | 8/2014 | Beaupre et al. |
| 2014/0324007 A1 | 10/2014 | Hundorf et al. |
| 2015/0096700 A1 | 4/2015 | Heiskanen |
| 2015/0099086 A1 | 4/2015 | Kim |
| 2015/0114581 A1 | 4/2015 | Kinnunen |
| 2015/0118466 A1 | 4/2015 | Zwick |
| 2015/0144829 A1 | 5/2015 | Grünbauer |
| 2015/0176221 A1 | 6/2015 | Maladen |
| 2015/0284911 A1 | 10/2015 | Juvonen et al. |
| 2016/0219810 A1 | 8/2016 | Erkkilä et al. |
| 2016/0353820 A1 | 12/2016 | Baychar |
| 2017/0335521 A1 | 11/2017 | Lee |
| 2017/0335522 A1 | 11/2017 | Heiskanen et al. |
| 2017/0362775 A1 | 12/2017 | Juvonen et al. |
| 2018/0119353 A1 | 5/2018 | Tolfsson et al. |
| 2018/0327973 A1 | 11/2018 | Siitonen et al. |
| 2018/0355527 A1 | 12/2018 | Strandqvist et al. |
| 2019/0161915 A1 | 5/2019 | Swails et al. |

FOREIGN PATENT DOCUMENTS

| | | |
|---|---|---|
| AT | 519423 A3 | 8/2018 |
| AU | 281485 B | 2/1965 |
| AU | 1973057198 A | 1/1975 |
| AU | 700394 B2 | 1/1999 |
| AU | 721197 B2 | 6/2000 |
| AU | 2002300959 | 6/2003 |
| AU | 2001285005 B2 | 2/2006 |
| AU | 2007272602 A1 | 1/2008 |
| AU | 2012298266 B2 | 6/2016 |
| BE | 436451 A | 9/1939 |
| CA | 949706 A | 6/1974 |
| CA | 979699 A | 12/1975 |
| CA | 2194176 A1 | 12/1996 |
| CA | 2868935 A1 | 9/2014 |
| CA | 2998561 A1 | 3/2018 |
| CN | 1173122 A | 2/1998 |
| CN | 1260977 A | 7/2000 |
| CN | 1270648 A | 10/2000 |
| CN | 1364182 A | 8/2002 |
| CN | 1094542 C | 11/2002 |
| CN | 1518423 A | 8/2004 |
| CN | 1555431 A | 12/2004 |
| CN | 101410078 B | 2/2014 |
| CN | 103993498 B | 3/2016 |
| CN | 105828763 A | 8/2016 |
| CN | 105828764 A | 8/2016 |
| CN | 105899173 A | 8/2016 |
| CN | 104302834 B | 11/2016 |
| CN | 106456416 A | 2/2017 |
| CN | 107460764 A | 12/2017 |
| CN | 107988838 A | 5/2018 |
| CN | 109937027 A | 6/2019 |
| DE | 2041406 A1 | 4/1971 |
| DE | 2438587 A1 | 3/1975 |
| DE | 2902255 A1 | 7/1980 |
| DE | 3307736 A1 | 9/1984 |
| DE | 3420195 C2 | 6/1987 |
| DE | 4207233 A1 | 11/1993 |
| EP | 0101319 A3 | 3/1984 |
| EP | 0049944 B1 | 11/1984 |
| EP | 0136329 A4 | 1/1989 |
| EP | 0158938 B1 | 12/1989 |
| EP | 0296242 A4 | 7/1991 |
| EP | 0443082 A1 | 8/1991 |
| EP | 0242361 B1 | 9/1991 |
| EP | 0512819 A1 | 11/1992 |
| EP | 0150777 B2 | 11/1994 |
| EP | 0481745 B1 | 7/1996 |
| EP | 0537005 B1 | 7/1997 |
| EP | 0671504 B1 | 8/1997 |
| EP | 0742858 B1 | 6/1999 |
| EP | 1007784 B1 | 2/2003 |
| EP | 1145695 A3 | 1/2004 |
| EP | 1194644 B1 | 3/2004 |
| EP | 1400224 B1 | 3/2006 |
| EP | 1384457 B1 | 5/2006 |
| EP | 1808116 A1 | 7/2007 |
| EP | 1649094 B1 | 9/2007 |
| EP | 1442173 B1 | 3/2008 |
| EP | 1583865 B1 | 5/2008 |
| EP | 1463432 B1 | 8/2008 |
| EP | 1576233 B1 | 10/2008 |
| EP | 1813237 A3 | 12/2008 |
| EP | 1932968 B1 | 9/2009 |
| EP | 1967626 A4 | 9/2009 |
| EP | 1666240 B1 | 3/2011 |
| EP | 1440195 B1 | 8/2011 |
| EP | 1812637 B1 | 1/2012 |
| EP | 1950343 B1 | 4/2012 |
| EP | 1456472 B2 | 5/2012 |
| EP | 1497489 B1 | 8/2012 |
| EP | 1808152 B1 | 8/2012 |
| EP | 1567718 B1 | 4/2013 |
| EP | 2599915 A1 | 6/2013 |
| EP | 1268937 B1 | 2/2014 |
| EP | 2540892 B1 | 4/2014 |
| EP | 1876291 B1 | 9/2014 |
| EP | 2843130 A1 | 3/2015 |
| EP | 2952164 A1 | 12/2015 |
| EP | 2952165 A1 | 12/2015 |
| EP | 2737131 B1 | 1/2016 |
| EP | 1916333 B1 | 6/2016 |
| EP | 2001662 B1 | 6/2016 |
| EP | 1380401 B1 | 7/2016 |

(56) References Cited

FOREIGN PATENT DOCUMENTS

| | | |
|---|---|---|
| EP | 2807212 B1 | 4/2017 |
| EP | 2940210 B1 | 8/2017 |
| EP | 2622132 B1 | 4/2018 |
| EP | 3327395 A1 | 5/2018 |
| EP | 3162956 B1 | 3/2019 |
| EP | 3108060 B1 | 4/2021 |
| ES | 385106 A1 | 3/1973 |
| ES | 8606100 A1 | 4/1986 |
| ES | 2362723 T3 | 7/2011 |
| FI | 812601 A | 2/1982 |
| FI | 843904 A | 10/1984 |
| FI | 83741 C | 12/1992 |
| FI | 112812 B | 1/2004 |
| FI | 127377 B | 4/2018 |
| FI | 128917 B | 3/2021 |
| FR | 873763 A | 7/1942 |
| FR | 1449737 A | 8/1966 |
| FR | 1528992 A | 6/1968 |
| FR | 2206398 B3 | 9/1976 |
| GB | 1145484 A | 3/1969 |
| GB | 2109023 A | 5/1983 |
| GB | 2136813 A | 9/1984 |
| GB | 2116882 B | 10/1985 |
| IN | 1182DEL2005 A | 1/2007 |
| IN | 231170 B | 3/2009 |
| IN | 2957KOLNP2014 A | 5/2015 |
| IN | 3108MUM2014 A | 4/2016 |
| IN | 283291 B | 5/2017 |
| IN | 201717030330 A | 12/2017 |
| IN | 201837033267 A | 10/2018 |
| JP | 1983115199 A | 7/1983 |
| JP | 1989501859 A | 6/1989 |
| JP | 1993140886 A | 6/1993 |
| JP | 2010215872 A2 | 9/2010 |
| JP | 2014037652 A2 | 2/2014 |
| KR | 1020040088545 A | 10/2004 |
| KR | 100450272 B1 | 12/2005 |
| KR | 100637646 B1 | 10/2006 |
| KR | 100685522 B1 | 2/2007 |
| KR | 100725240 B1 | 6/2007 |
| KR | 1020100112299 A | 10/2010 |
| KR | 1020130077856 A | 7/2013 |
| KR | 101386319 B1 | 4/2014 |
| KR | 1020180007337 A | 1/2018 |
| RU | 2393093 C2 | 6/2010 |
| SE | 7304825 L | 11/1977 |
| SE | 7304888 L | 11/1977 |
| SE | 412881 B | 3/1980 |
| SE | 1651412 A1 | 4/2018 |
| SE | 540719 C2 | 10/2018 |
| WO | 1986003505 A1 | 6/1986 |
| WO | 1991010416 A1 | 7/1991 |
| WO | 1992003283 A1 | 3/1992 |
| WO | 1996031652 A1 | 10/1996 |
| WO | 9637138 A1 | 11/1996 |
| WO | 9824621 A1 | 6/1998 |
| WO | 2000001882 A1 | 1/2000 |
| WO | 2000050694 A1 | 8/2000 |
| WO | 0112902 A1 | 2/2001 |
| WO | 2001068793 A1 | 9/2001 |
| WO | 2001083866 A2 | 11/2001 |
| WO | 02055788 A2 | 7/2002 |
| WO | 2002055788 A2 | 7/2002 |
| WO | 2003069038 A1 | 8/2003 |
| WO | 2004025009 A2 | 3/2004 |
| WO | 2004112956 A1 | 12/2004 |
| WO | 2005060712 A2 | 7/2005 |
| WO | 2006052967 A2 | 5/2006 |
| WO | 2006094077 A2 | 9/2006 |
| WO | 2007074625 A1 | 7/2007 |
| WO | 07110497 A2 | 10/2007 |
| WO | 08027488 A2 | 3/2008 |
| WO | 2009006371 A2 | 1/2009 |
| WO | 2009060118 A2 | 5/2009 |
| WO | 2011104427 A1 | 9/2011 |
| WO | 12006714 A1 | 1/2012 |
| WO | 14080084 A1 | 5/2014 |
| WO | 2014068196 A2 | 5/2014 |
| WO | 2014080084 A1 | 5/2014 |
| WO | 14202841 A1 | 12/2014 |
| WO | 2014205048 A1 | 12/2014 |
| WO | 15036659 A1 | 3/2015 |
| WO | 15066036 A1 | 5/2015 |
| WO | 15080726 A1 | 6/2015 |
| WO | 2015083092 A1 | 6/2015 |
| WO | 2015112155 A1 | 7/2015 |
| WO | 2015173474 A1 | 11/2015 |
| WO | 2016050901 A1 | 4/2016 |
| WO | 2016051350 A1 | 4/2016 |
| WO | 2016185398 A1 | 11/2016 |
| WO | 2016200299 A1 | 12/2016 |
| WO | 2017006216 A1 | 1/2017 |
| WO | 2017006241 A1 | 1/2017 |
| WO | 2017046751 A1 | 3/2017 |
| WO | 17079169 A1 | 5/2017 |
| WO | 17079310 A1 | 5/2017 |
| WO | 2017079169 A1 | 5/2017 |
| WO | 2017137879 A1 | 8/2017 |
| WO | 2018002815 A1 | 1/2018 |
| WO | 2018011667 A1 | 1/2018 |
| WO | 2018041355 A1 | 3/2018 |
| WO | 2018065668 A1 | 4/2018 |
| WO | 2018116223 A1 | 6/2018 |
| WO | 2018152082 A1 | 8/2018 |
| WO | 2018171913 A1 | 9/2018 |
| WO | 2018171914 A1 | 9/2018 |

\* cited by examiner

PAPER TISSUE WITH HIGH BULK AND LOW LINT

This application claims the benefit of priority from U.S. Provisional Application No. 62/250,242 filed on Nov. 3, 2015, the contents of which are incorporated herein by reference.

BACKGROUND

Wood pulp fiber is a natural fiber widely used in personal care products such as facial tissue, toilet paper, paper hand towels, cosmetic wipes, etc. Wood pulp fiber is a relatively inexpensive raw material and is widely available. In addition, wood pulp fibers have various advantageous properties such as being highly absorbent, relatively soft and biodegradable. However, these desirable properties are often lost or degraded as a result of the sheet formation process. In this regard, wood pulp fibers have a relatively short fiber length, commonly between about 0.5-2 mm, which makes it difficult to achieve both the desired fiber orientation and structure (i.e. to achieve a high-bulk sheet having good hand and flexibility) and also the desired degree of sheet integrity and fiber retention (i.e. to achieve a stable structure and minimize linting).

Wood pulp fiber is typically incorporated into a sheet by either an air laying or wet laying process. With respect to cellulosic sheets formed by air laying process, sheets formed from such processes tend to have a high bulk as the air-laying processes typically achieve an open and non-oriented fiber structure. However, such air-laid sheets also tend to suffer from low integrity and high lint due to the lack of hydrogen bonding as between the individual fibers. While sheet integrity and linting can be improved through the addition of significant levels of binder fibers or adhesive, the inclusion of the same often causes the sheet to lose desired attributes such as softness, drape and other properties such as biodegradability and/or flushability.

On the other hand, with respect to wood pulp fibers processed by a wet laying process, the resulting sheets often have relatively low lint content due to the extensive hydrogen bonding between wood pulp fibers. However, the wet laid sheets sacrifice bulk and wet integrity due to the generally planar and compact fiber orientation.

Therefore, it would be desirable to have a paper tissue sheet comprising wood pulp or like cellulosic fibers and minimal binder having a combination of advantageous properties such as sheet integrity, high bulk and low lint content.

SUMMARY OF INVENTION

The present invention provides a tissue paper product having at least one ultra-low density ply having a highly porous, open-celled structure and that comprises cellulosic fibers, a water insoluble binder and a foaming surfactant. The cellulosic fiber comprises greater than 50% by weight of the ply and are bonded to one another by hydrogen bonding. Further, the ply has a density less than about 0.04 g/cc and yet still provides a Gelbo Lint Value less than 5 and a wet tensile strength of at least 10 g-f. In certain embodiments, the ply has a substantially planar, sheet-like structure having a thickness of between about 0.5 and about 5 mm. In addition, water insoluble binders, such as binder fibers, comprise less than about 10% of the ply. In certain embodiments, the tissue paper product can further include one or more additional plies, attached to the ultra-low density ply, comprising a wet-laid tissue including at least 95% wood pulp fibers and having a density between about 0.5 and 0.04 g/cc. Further, one or more of the plies may be pattern embossed, either individually or together with other plies.

In one embodiment, the tissue product may be utilized as part of a wiper and included within a packaged wiping product. In this regard, a packaged wipes product is also provided having a container that defines an interior space and that houses a stack of between 3 and 150 individual wipers. The individual wipers within the container include one or more layers of the ultra-low density tissue sheets described herein. In certain embodiments the packaged wiping product can comprise a stack of wipers provided in a roll format having individual wipers separated by lines of perforation or in a superposed format having wipers in an inter-folded relationship. In still a further embodiment, the ultra-low density tissue sheets may be employed as or part of an absorbent core or liquid distribution layer of a personal care absorbent product such as, for example, a diaper, panty-liner and so forth.

FIGURES

DESCRIPTION

Figure 1:
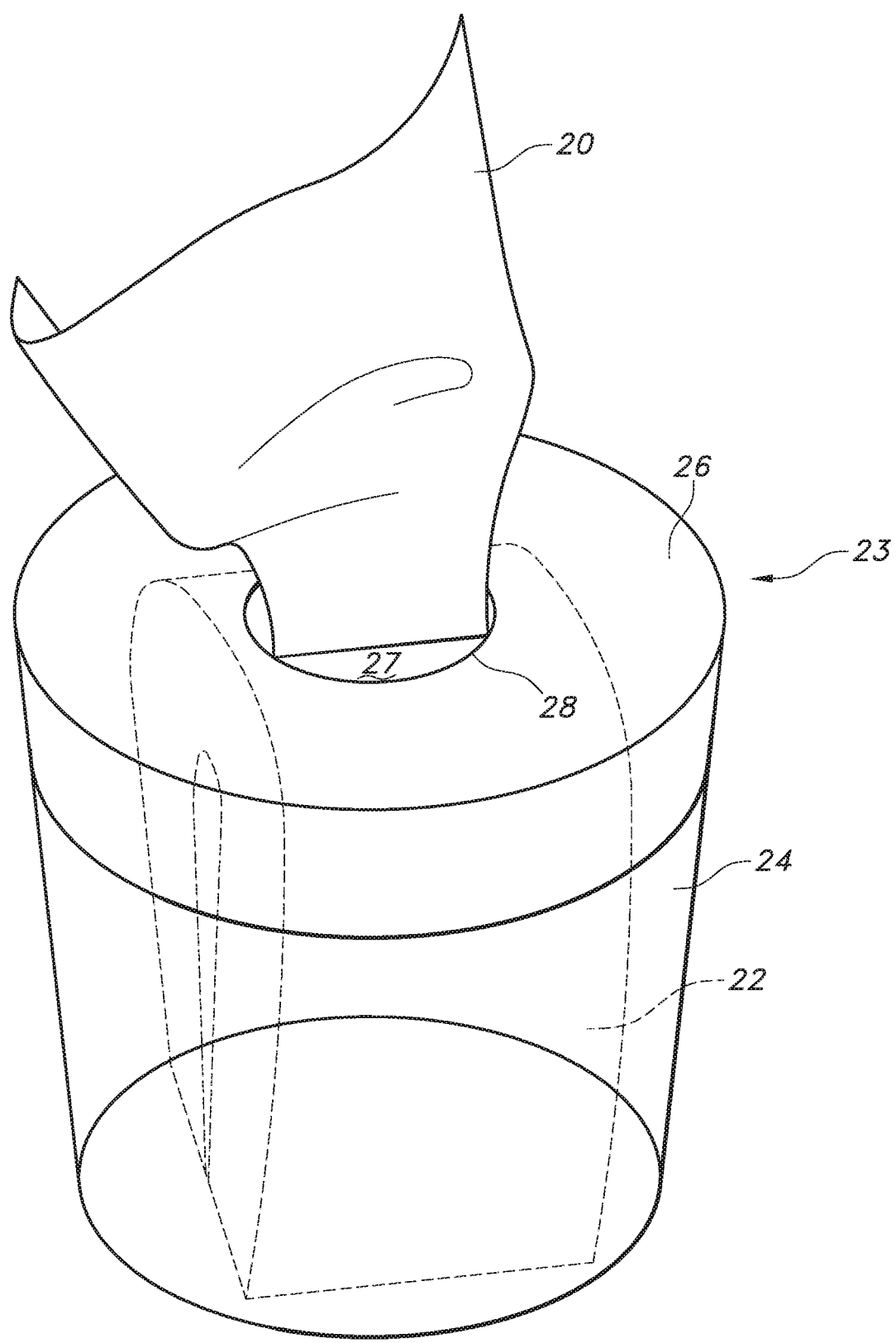
FIG. 1 is a perspective view of a dispenser housing a stack of tissue sheets of the present invention.

The ultra-low density paper tissue webs of the present invention are made by forming a highly-expanded, highly porous foam from a foam precursor or slurry comprising (i) a foaming fluid; (ii) cellulosic fibers; (iii) foaming surfactant and, optionally one or more (iv) binders; (v) foam stabilizers; (vi) strength enhancing agents; or (vii) additional additives.

Foaming Fluid

Any one or more known foaming fluids compatible with the other components may be used in the practice of the present invention. Suitable foaming fluids include, but are not limited to, water and so forth. The foaming fluid can comprise between about 90% and about 99.9% % of the slurry. In certain embodiments the foaming fluid can comprise between about 93% and 99.5% of the slurry or even between about 95% and about 99.0% of the slurry.

Cellulosic Fibers

A wide variety of cellulosic fibers are believed suitable for use herein. The ultra-low density cellulosic webs of the present invention can, in one aspect, comprise conventional papermaking fibers such as wood pulp fibers formed by a variety of pulping processes, such as kraft pulp, sulfite pulp, bleached chemithermomechanical pulp (BCTMP), chemithermomechanical pulp (CTMP), pressure/pressure thermomechanical pulp (PIMP), thermomechanical pulp (TMP), thermomechanical chemical pulp (TMCP), and so forth. By way of example only, fibers and methods of making wood pulp fibers are disclosed in U.S. Pat. No. 4,793,898 to Laamanen et al.; U.S. Pat. No. 4,594,130 to Chang et al.; U.S. Pat. No. 3,585,104 to Kleinhart; U.S. Pat. No. 5,595,628 to Gordon et al.; U.S. Pat. No. 5,522,967 to Shet; and so forth. Further, the fibers may be any high-average fiber length wood pulp, low-average fiber length wood pulp, or mixtures of the same. Examples of suitable high-average length pulp fibers include softwood fibers, such as, but not limited to, northern softwood, southern softwood, redwood, red cedar, hemlock, pine (e.g., southern pines), spruce (e.g., black spruce), combinations thereof, and the like. Examples of suitable low-average length pulp fibers include hardwood fibers, such as, but not limited to, eucalyptus, maple, birch, aspen, and the like.

Moreover, if desired, secondary fibers obtained from recycled materials may be used, such as fiber pulp from sources such as, for example, newsprint, reclaimed paperboard, and office waste. In a particularly preferred embodiment refined fibers are utilized in the tissue web such that the total amount of virgin and/or high average fiber length wood fibers, such as softwood fibers, may be reduced.

Regardless of the origin of the wood pulp fiber, the wood pulp fibers preferably have an average fiber length greater than about 0.2 mm and less than about 3 mm, such as from about 0.35 mm and about 2.5 mm, or between about 0.5 mm to about 2 mm or even between about 0.7 mm and about 1.5 mm.

In addition, other cellulosic fibers believed suitable for use in making the cellulosic webs of the present invention include nonwoody fibers, such as cotton, abaca, bambo, kenaf, sabai grass, flax, esparto grass, straw, jute hemp, bagasse, milkweed floss fibers, and pineapple leaf fibers. In addition other cellulosic fibers for making the tissue webs include synthetic cellulose fiber types including rayon in all its varieties and other fibers derived from viscose or chemically-modified cellulose such as, for example, those available under the trade names LYOCELL and TENCEL. The non-woody and synthetic cellulosic fibers can have fiber length greater than about 0.2 mm including, for example, having an average fiber size between about 0.5 mm and about 50 mm or between about 0.75 and about 30 mm or even between about 1 mm and about 25 mm. Generally speaking, when fibers of relatively larger average length are being used, it will often be advantageous to utilize relatively higher amounts of foaming surfactant in order to help achieve a foam with the required stability.

The solids content, including the cellulosic fibers and any other fibers or particulates contained herein, desirably comprise no more than about 15% of the slurry. In certain embodiments the cellulosic fibers can comprise between about 0.1% and about 15% of the slurry or between about 0.2 and about 10% of the slurry or even between about 0.5% and about 8% of the slurry.

Foaming Surfactant

The ultra-low density paper tissue webs of the present invention are made utilizing one of more surfactants capable of forming a stable, high-expansion foam. The fibers and surfactant, together with the foaming liquid and any additional components, need to form a stable dispersion capable of substantially retaining a high degree of porosity for longer that the drying process. In this regard, the surfactant is selected so as to provide a foam slurry having a stability of at least 15 minutes, and still more desirably at least 30 minutes. The foaming surfactant used in the slurry can be selected from one or more known in the art that are capable of providing the desired degree of foam stability. In this regard, the foaming surfactant can be selected from anionic, cationic, nonionic and amphoteric surfactants provided they, alone or in combination with other components, provide the necessary foam stability. As will be appreciated, more than one surfactant can be used, including both different types of surfactants and more than one surfactant of the same type.

Anionic surfactants believed suitable for use with the present invention include, without limitation, anionic sulfate surfactants, alkyl ether sulfonates, alkylaryl sulfonates, or mixtures or combinations thereof. Examples of alkylaryl sulfonates include, without limitation, alkyl benzene sulfonic acids and their salts, dialkylbenzene disulfonic acids and their salts, dialkylbenzene sulfonic acids and their salts, alkylphenol sulfonic acids/condensed alkylphenol sulfonic acids and their salts, or mixture or combinations thereof. Examples of additional anionic surfactants believed suitable for use in the present invention include alkali metal sulforicinates, sulfonated glyceryl esters of fatty acids such as sulfonated monoglycerides of coconut oil acids, salts of sulfonated monovalent alcohol esters such as sodium oleylisethianate, metal soaps of fatty acids, amides of amino sulfonic acids such as the sodium salt of oleyl methyl tauride, sulfonated products of fatty acids nitriles such as palmitonitrile sulfonate, alkali metal alkyl sulfates such as sodium lauryl sulfate, ammonium lauryl sulfate or triethanolamine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, sulphuric esters of polyoxyethylene alkyl ether, sodium salts, potassium salts, and amine salts of alkylnapthylsulfonic acid. Certain phosphate including phosphate esters such as sodium lauryl phosphate esters or those available from the Dow Chemical Company under the tradename TRITON are also believed suitable for use herewith. A particularly effective anionic surfactant is sodium dodecyl sulfate (SDS).

Cationic surfactants are also believed suitable for use with the present invention. Foaming cationic surfactants include, without limitation, monocarbyl ammonium salts, dicarbyl ammonium salts, tricarbyl ammonium salts, monocarbyl phosphonium salts, dicarbyl phosphonium salts, tricarbyl phosphonium salts, carbylcarboxy salts, quaternary ammonium salts, imidazolines, ethoxylated amines, quaternary phospholipids and so forth. Examples of additional cationic surfactants include various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines such as undecylimidazoline, fatty amides derived from disubstituted amines such as oleylaminodiethylamine, derivatives of ethylene diamine, quaternary ammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides, dioctadecyldimethylammonium hydroxide, tallow trimethylammonium hydroxide, trimethylammonium hydroxide, methylpolyoxyethylene cocoammonium chloride, and dipalmityl hydroxyethylammonium methosulfate, amide derivatives of amino alcohols such as beta-hydroxylethyl-stearylamide, and amine salts of long chain fatty acids. Further examples of cationic surfactants believed suitable for use with the present invention include benzalkonium chloride, benzethonium chloride, cetrimonium bromide, distearyldimethylammonium chloride, tetramethylammonium hydroxide, and so forth.

Nonionic surfactants believed suitable for use in the present invention include, without limitation, condensates of ethylene oxide with a long chain fatty alcohol or fatty acid, condensates of ethylene oxide with an amine or an amide, condensation products of ethylene and propylene oxides, fatty acid alkylol amide and fatty amine oxides. Various examples of non-ionic surfactants include stearyl alcohol, sorbitan monostearate, octyl glucoside, octaethylene glycol monododecyl ether, lauryl glucoside, cetyl alcohol, cocamide MEA, monolaurin, polyoxyalkylene alkyl ethers such as polyethylene glycol long chain (12-14C) alkyl ether, polyoxyalkylene sorbitan ethers, polyoxyalkylene alkoxylate esters, polyoxyalkylene alkylphenol ethers, ethylene glycol propylene glycol copolymers, polyvinyl alcohol, alkylpolysaccharides, polyethylene glycol sorbitan monooleate, octylphenol ethylene oxide, and so forth.

The foaming surfactant can be used in varying amounts as necessary to achieve the desired foam stability and air-content. In certain embodiments, the foaming surfactant can comprise between about 0.01% and about 5% of the slurry. In certain embodiments the foaming surfactant can comprise between about 0.05% and about 3% of the slurry or even between about 0.1% and about 2% of the slurry.

Foam Stabilizers

The foam pre-cursor or slurry may optionally also include one or more foam stabilizers known in the art and that are compatible with the components of the slurry and further do not interfere with the hydrogen bonding as between the cellulosic fibers. Foam stabilizing agents believed suitable for use in the present invention, without limitation, one or more zwitterionic compounds, amine oxides, alkylated polyalkylene oxides, or mixture or combinations thereof. Specific examples of foam stabilizers includes, without limitation, cocoamine oxide, isononyldimethylamine oxide, n-dodecyldimethylamine oxide, and so forth. The foam stabilizer can comprise between about 0.01% and about 2% of the slurry. In certain embodiments the foam stabilizer can comprise between about 0.05% and 1% of the slurry or even between about 0.1 and about 0.5% of the slurry.

Binder

Binder materials include suitable for use in the present invention include, but are not limited to, thermoplastic binder fibers and water-compatible adhesives such as, for example, latexes. Importantly, the binder will comprise one that is water insoluble on the dried cellulosic web. In certain embodiments, latexes used in the present invention can be cationic or anionic to facilitate application to and adherence to the cellulosic fiber. For instance, latexes believed suitable for use with the present invention include, but are not limited to, anionic styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, as well as other suitable anionic latex polymers known in the art. Examples of such latexes are described in U.S. Pat. No. 4,785,030 to Hager, U.S. Pat. No. 6,462,159 to Hamada, U.S. Pat. No. 6,752,905 to Chuang et al. and so forth. Examples of suitable thermoplastic binder fibers include, but are not limited to, monocomponent and multi-component fibers having at least one relatively low melting thermoplastic polymer such as polyethylene. In certain embodiments, polyethylene/polypropylene sheath/core staple fibers can be used. Binder fibers may have lengths described herein above in relation to the synthetic cellulosic fibers.

Binders in liquid form, such as latex emulsions, can comprise between about 0% and about 10% of the slurry. In certain embodiments the non-fibrous binder can comprise between about 0.1% and 10% of the slurry or even between about 0.2% and about 5% or even between about 0.5% and about 2% of the slurry. Binder fibers, when used, may be added proportionally to the other components to achieve the desired fiber ratios and structure while maintaining the total solids content of the slurry below the amounts stated above.

Strength Additives

One or more wet strength additives may, optionally, be added to the slurry in order to help improve the relative strength of the ultra-low density paper tissue sheet. Such strength additives suitable for use with paper making fibers and the manufacture of paper tissue are known in the art.

Temporary wet strength additives may be cationic, non-ionic or anionic. Examples of such temporary wet strength additives include PAREZ™ 631 NC and PAREZ® 725 temporary wet strength resins that are cationic glyoxylated polyacrylamides available from Cytec Industries, located at West Paterson, N.J. These and similar resins are described in U.S. Pat. No. 3,556,932 to Coscia et al. and U.S. Pat. No. 3,556,933 to Williams et al. Additional examples of temporary wet strength additives include dialdehyde starches and other aldehyde containing polymers such as those described in U.S. Pat. No. 6,224,714 to Schroeder et al.; U.S. Pat. No. 6,274,667 to Shannon et al.; U.S. Pat. No. 6,287,418 to Schroeder et al.; and U.S. Pat. No. 6,365,667 to Shannon et al., and so forth.

Permanent wet strength agents comprising cationic oligomeric or polymeric resins may be used in the present invention. Polyamide-polyamine-epichlorohydrin type resins such as KYMENE 557H sold by Hercules, Inc. located at Wilmington, Del. are the most widely used permanent wet-strength agents and are suitable for use in the present invention. Such materials have been described in the following U.S. Pat. No. 3,700,623 to Keim; U.S. Pat. No. 3,772,076 to Keim; U.S. Pat. No. 3,855,158 to Petrovich et al.; U.S. Pat. No. 3,899,388 to Petrovich et al.; U.S. Pat. No. 4,129,528 to Petrovich et al.; U.S. Pat. No. 4,147,586 to Petrovich et al.; U.S. Pat. No. 4,222,921 to van Eenam and so forth. Other cationic resins include polyethylenimine resins and aminoplast resins obtained by reaction of formaldehyde with melamine or urea. Permanent and temporary wet strength resins may be used together in the manufacture of tissue sheets and tissue products of the present invention.

Dry strength resins may also optionally be applied to the tissue sheet of the present invention. Such materials may include, but are not limited to, modified starches and other polysaccharides such as cationic, amphoteric, and anionic starches and guar and locust bean gums, modified polyacrylamides, carboxymethylcellulose, sugars, polyvinyl alcohol, chitosan, and the like.

The strength additives can comprise between about 0.01 and about 5% of the slurry. In certain embodiments the strength additives can comprise between about 0.05% and about 2% of the slurry or even between about 0.1% and about 1% of the slurry.

Additional Additives.

Other additional components may be added to the slurry so long as they do significantly interfere with the formation of the highly-expanded stable foam, the hydrogen bonding as between the cellulosic fibers or other desired properties of the web. As examples, additional additives may include one or more pigments, opacifying agents, anti-microbial agents, pH modifiers, skin benefit agents, fragrances and so forth as desired to impart or improve one or more physical or aesthetic attributes. In certain embodiments the tissue sheet may include skin benefit agents such as, for example, antioxidents, astringents, conditioners, emollients, deodorants, external analgesics, film formers, humectants, hydrotropes, pH modifiers, surface modifiers, skin protectants, and so forth. When employed, miscellaneous additives desirably comprise less than about 2% of the slurry and still more desirably less than about 1% of the slurry and even less than about 0.5% of the slurry.

Formation of the Tissue Sheet
Formation of Highly-Expanded Foam

The foam precursor or slurry is acted upon to form a highly-expanded foam. More specifically, the slurry is acted upon so as to form a highly porous foam having an air content greater than about 50% by volume and, more desirably, greater than about 60% by volume. In certain aspects, the highly-expanded foam is formed having an air content of between about 60% and about 95% and in further aspects between about 65% and about 85% by volume. In certain embodiments, the highly-expanded foam may be acted upon to introduce air bubbles such that the ratio of expansion (volume of air to slurry in the expanded stable foam) is greater than 1:1 and in certain embodiments the ratio of slurry:air can be between about 1:1.1 and about 1:20 or between about 1:1.5 and about 1:15 or between about 1:2 and about 1:10 or even between about 1:3 and about 1:5.

The highly-expanded foam can be generated by one or more means known in the art. Examples of suitable methods include, without limitation, aggressive mechanical agitation, injection of compressed air, and so forth. Mixing the components through the use of a high-shear, high-speed mixer is particularly well suited for use in the formation of the desired highly-porous foams. Various high-shear mixers are known in the art and believed suitable for use with the present invention. High-shear mixers typically employ a tank holding the foam precursor and/or one or more pipes through which the foam precursor is directed. The high-shear mixers may use a series of screens and/or rotors to work the precursor and cause aggressive mixing of the components and air. In a particular embodiment, a tank is provided having therein one or more rotors or impellors and associated stators. The rotors or impellors are rotated at high speeds in order to cause flow and shear as a result of the speed of the slurry at the tip of the rotor being higher than that at the center of the rotor. Air may, for example, be introduced into the tank at various positions or simply drawn in by the action of the mixer. While the specific mixer design may influence the speeds necessary to achieve the desired mixing and shear, in certain embodiments suitable rotor speeds may be at least about 1000 rpm and, for example, be between about 1000 rpm and about 6000 rpm or between about 2000 rpm and about 4000 rpm. In certain embodiments, with respect to rotor based high-shear mixers, the mixer maybe run with the foam slurry until the disappearance of the vertex in the slurry.

In addition, it is noted the foaming process can be accomplished in a single foam generation step or in sequential foam generation steps. For example, in one embodiment, all of the components may be mixed together to form a foam slurry from which a highly-expanded foam is formed. Alternatively, one or more of the individual components may be added to the foaming fluid, an initial mixture formed (e.g. a dispersion or foam), after which the remaining components may be added to the initially foamed slurry and then acted upon to form the final highly-expanded foam. In this regard, the water and foaming surfactant may be initially mixed and acted upon to form an initial foam. The cellulosic fibers may then be added to the water/surfactant foam and then further acted upon to form the final highly-expanded foam. As a further alternative, the water and fibers may be aggressively mixed to form an initial dispersion after which the foaming surfactant and other components are added to form a second mixture which is then mixed and acted upon to form the highly-expanded foam.

Tissue Sheet Formation

The highly-expanded foam, once formed, can be acted upon so as to remove the foaming fluid, without substantial loss or degradation of the porous structure, so as to form an ultra-low density paper tissue web. Typically, this will comprise drying of the highly-expanded foam in a non-compressive manner. The highly-expanded foam can be dried by one or more means known in the art such as, for example, heating by radiation such as microwaves or infrared radiation, inductively heated, heated by conduction or convection, such as by gentle (non-compressive) through-air drying, or the like. As an example, and with respect to through-air drying, the highly-expanded foam can be fed onto a foraminous fabric or screen (i.e. a forming fabric) and hot, dry air directed though the foam. In this regard, desirable flow rates are sufficiently low so as not to cause significant compression and/or degradation of the air bubbles strewn throughout the material. Alternatively, a sheet of high-expanded foam can be placed into a convection oven and heated to the desired degree. It will be appreciated that temperatures used in the drying operation should not be so high as to excessively melt any binder fiber that may be present nor so high as to cause significant loss of air bubbles within the material. The foam is desirably dried to achieve a paper tissue web wherein less than about 10% of the foaming liquid and/or water remains. In certain embodiments, the dried paper tissue web will have a water content of between about 1% and about 8% or further between about 2% and 5%.

In one aspect, the highly-expanded foam may be directed onto and spread across a forming fabric or mold to form a sheet-like structure. The spread and height of the foam will be selected in relation and/or proportional to the desired dimensions of the dried cellulosic web.

Cellulosic Product

Once dried, the cellulosic tissue sheet of the present invention will have very low densities, such as below 0.5 g/cc. In this regard, the cellulosic tissue sheet can have a density below about 0.04 g/cc such as for example, having a density between about 0.04 g/cc and about 0.005 g/cc, between about 0.02 g/cc and about 0.005 g/cc or even between about 0.099 g/cc and about 0.005 g/cc. Relatedly, in certain aspects, the cellulosic tissue sheet can comprise a highly porous structure having network of inter-connected pores extending through the thickness of the sheet. In certain embodiments, a significant number and/or majority of pores having a substantially spherical shape.

Further, the cellulosic tissue sheet can comprise greater than 50% by wt. cellulosic fibers and in certain embodiments can comprise greater than 70%, 85%, or even 95% by wt. cellulosic fibers. In certain embodiments, the cellulosic fibers can comprise 100% of the fibrous component of the tissue sheet including, for example, comprising between about 55%-100% by wt. or between about 85%-100% by wt. of the fibrous component of the tissue sheet. Further, in certain embodiments, the cellulosic tissue sheet can include less than about 30%, less than 10% or less than 2% by wt. binder. In certain embodiments, the tissue sheet can include, for example, between 0-30% by wt. binder, between 0.1%-10% or between about 0.1%-2% by wt. binder.

Depending on the method of drying the foam, a portion of the foaming surfactant may have been removed with the water. However, regardless of the drying method, an amount of foaming surfactant will remain on the fibers and within the foamed tissue sheet. In this regard, the cellulosic tissue web can include between about 0.01% and about 5% by wt. foaming surfactant. In certain embodiments the tissue sheet can comprise between about 0.05% and about 3% or between about 0.5% and 3% or even between about 0.1% and about 1% by wt. foaming surfactant. Similarly, the foam stabilizer, when used, may be present in the dried paper tissue web in an amount between 0 and about 2% by wt., or between about 0.01% and about 2% by wt. or even between about 0.05% and about 1% by wt. Further, the strength enhancing agents, when used, may be present in the cellulosic tissue sheet in an amount between about 0.01% and about 5% by wt. and in other embodiments between about 0.5% and about 2% by wt.

In addition, despite the ultra-low density of the sheet and high cellulosic fiber content, it can have low lint properties. More specifically, the tissue sheet can have Gelbo Lint Value Gelbo Lint Value less than 5 and more desirably less than 4 and still more desirably less than 3. In certain embodiments, for particles having a size of at least 0.10 mm, the tissue sheet can have a modified Gelbo Lint Value of less than 5 and more desirably less than 4 and still more desirably less than 3. Further, in certain embodiments, the cellulosic tissue sheet can have a wet tensile strength of at least about 10 g-f such as, for example, between about 15 and about 500 g-f or between about 20 and about 300 g-f.

The thickness and basis weight of the sheet can be selected as desired to fulfill the needs of the particular personal care article and/or component thereof. In this regard, the cellulosic tissue sheet can have a thickness selected to provide the desired degree of absorbency and/or bulk, and in certain aspects can have a thickness between about 0.5 and about 45 mm or, in alternate embodiments, between about 1 mm and 30 mm. The cellulosic tissue sheet may be converted into a wiping article, personal care article or a component of such articles through one or more known ways in the art. The size of the cellulosic tissue sheet may be shaped and/or sized as needed to provide sufficient bulk, surface area and/or perform the intended function either alone or as a component in a multi-component article.

Wiping Articles

With respect to uses as a wiping article such as, for example, as a facial tissue, cosmetic wipe, toilet tissue, table napkin, or other wiping article, the cellulosic tissue sheet can have a thickness of between about 0.5 mm and about 5 mm or, in other embodiments between about 1 mm about 3 mm. In certain embodiments, for wiping or cleaning applications and articles, the cellulosic tissue can have a basis weight of at least about 10 g/M$^2$ (or gsm) such as for example, having a basis weight of between about 10 gsm and about 100 gsm or between about 15 gsm and about 90 gsm or even between about 20 gsm and about 80 gsm.

With respect to a wiping and/or cleaning product, the size of the article 10 may be shaped and/or sized to provide sufficient surface area to enable a user to clean and/or treat the intended body part(s). By way of example, for many personal care applications it will be adequate for the article 10 to have a maximum diameter of between about 5-45 cm or, in other embodiments, between about 7 and about 35 cm or between about 10 cm and about 30 cm. For certain personal care products, including use as a facial cleansing and/or cosmetic product, the article 10 desirably has a length of between 5-30 cm and a width between about 5-30 cm, including for example, having dimensions between 25 cm (L)×25 cm (W) and (5 cm (L)×5 cm (W). The shape of the article 10 may vary as desired and may comprise rectilinear, curvilinear and irregular shapes. By way of example, the article may be circular, elliptical, oval, square, rectangular, multi-lobal and so forth.

Wiping and/or cleaning articles of the present invention can, in certain aspects, comprise multi-ply products wherein at least one of the layers comprises the ultra-low density cellulosic tissue web described herein. The individual layers may, in one aspect, be separately formed and then attached to one another by one or more means known in the art such as, for example, by adhesives, "crimp" or compressive bonding (e.g. application of pressure), thermal bonding (e.g. where a layer includes one or more thermoplastic binder fibers), and so forth. In one aspect, the multi-ply webs may be pattern embossed. Such embossing and/or plying techniques are known in the art and examples include, but are not limited to, those described in U.S. Pat. No. 3,867,225 Nystrand; U.S. Pat. No. 4,320,162 to Schulz; U.S. Pat. No. 305,181 to Veith and so forth. In addition and/or alternatively, the ultra-low density paper tissue web may be formed directly on or with a second layer to form an integrated and/or coherent multi-layer laminate.

In certain aspects, the tissue product may comprise a multi-layer or multi-ply product comprising a first tissue web comprising an ultra-low density tissue web as described herein and a second paper tissue web having one or more different properties from that of the ultra-low density paper tissue web. In one aspect, the second paper tissue web can have a density of between 0.5 g/cc and 0.04 g/cc or, in further embodiments, a density between about 0.3 g/cc and about 0.05 g/cc. Further, the second tissue sheet can have a basis weight between about 10 to about 100 gsm or between about 20 and about 90 gsm. For certain facial tissue products, each of the layers can have a basis weight between about 10 to about 20 gsm. However, for heavier duty paper products such as a paper towel, in certain embodiments, each of the layers may have a basis weight between about 15 gsm and about 40 gsm. The thickness of the sheets may, in certain embodiments, be between about 0.5 mm and about 5 mm or, in other embodiments, between about 1 mm about 3 mm. The second ply can, in certain embodiments, comprise at least about 95% cellulosic fibers, at least about 98% cellulosic fibers or at least about 99% cellulosic fibers. Further, the fibers making up the second ply can, in certain embodiments, comprise entirely (100%) cellulosic fibers. The second ply can, in one aspect, comprise a wet-formed tissue sheet. Wet formed tissue sheets formed by a through-air drying process are well suited for use in conjunction with the foamed tissue sheet of the present invention; such tissue webs are generally characterized by relatively higher bulk and absorbency than convention wet-pressed tissue and in certain embodiments can be formed with a surface texture to improve cleaning efficacy and/or hand. Tissue sheets of this type are described in and formed by methods described in U.S. Pat. No. 4,191,609 to Trokhan; U.S. Pat. No. 5,443,691 to Van Phan et al.; U.S. Pat. No. 5,672,248 to Wendt et al.; U.S. Pat. No. 6,787,000 Burazin et al.; US2015/0176221 Malden et al., and WO2015/080726 to Burazin et al.; the contents of which are incorporated herein by reference to the extent consistent herewith. Further, in certain embodiments the second web may comprise a wet-formed tissue sheet dried by a wet-press process and which is characterized by relatively higher density and more compact, planar fiber orientation. Such tissue webs are often dried on a Yankee drier and creped on one or both sides to further increase bulk and improve sheet strength. Tissue sheets of this type are described in and formed by methods described in U.S. Pat. No. 4,894,118 Edwards et al.; U.S. Pat. No. 4,942,077 Kessner et al.; U.S. Pat. No. 6,454,904 Hermans et al.; WO2015/066036 to Bradley et al., the contents of which are incorporated herein by reference to the extent consistent herewith.

In certain embodiments, the multi-ply tissue product of the present invention can comprise an ultra-low density tissue web as described herein attached to a nonwoven web. Nonwoven webs can be formed from many processes, such as, for example, meltblowing processes, spunbonding processes, air-laying processes, coforming processes, bonded carded web processes, hydroentangling processes and so forth. By way of non-limiting example, various nonwoven webs and processes for making the same are described in U.S. Pat. No. 3,849,241 to Butin et al., U.S. Pat. No. 4,340,563 to Appel et al., U.S. Pat. No. 4,443,513 to Meitner et al., U.S. Pat. No. 4,548,856 to Ali Kahn et al., U.S. Pat. No. 4,853,281 to Abba et al., U.S. Pat. No. 5,382,400 to Pike et al., U.S. Pat. No. 5,575,874 to Griesbach et al., U.S. Pat. No. 6,224,977 to Kobylivker et al., U.S. Pat. No. 6,811,638 to Close et al., U.S. Pat. No. 6,946,413 to Lange et al., US2004/0192136 to Gusky et al., US2006/0008621 to Gusky et al., U.S. Pat. No. 4,100,324 to Anderson et al., U.S. Pat. No. 5,350,624 to Georger et al., US2011/151596 to Jackson et al., U.S. Pat. No. 3,485,706 to Evans, U.S. Pat. No. 3,620,903 to Bunting et al., U.S. Pat. No. 5,009,747 Viazmensky et al., U.S. Pat. No. 5,284,703 to Everhart et al., U.S. Pat. No. 6,200,669 to Marmon et al., and so forth. In certain aspects the nonwoven webs can have a basis weight of from about 15 gsm to about 240 gsm or, in alternate embodiments, between about 20-190 gsm or between about 25-90 gsm. In this regard, the fibrous material includes greater than about 25% by weight synthetic fibers and in certain embodiments between about 40%-100% synthetic fibers and in still further embodiments between about 55%-100% synthetic fibers. The synthetic fibers may comprise polymers such as, for example, polyolefin, polyester, polyamide, polylactic acid, or other fiber forming polymers.

In a further aspect, a multi-ply product of the present invention can comprise an ultra-low density cellulosic tissue product as described herein plied to a nonwoven web of cellulosic synthetic fibers such as, for example, viscose. In one aspect, a multi-ply product can comprise an ultra-low density tissue product described herein attached to a biodegradable and/or flushable nonwoven web. Examples of biodegradable and/or flushable nonwoven fabrics include, but are not limited to, those described in U.S. Pat. No. 5,948,710 to Pomplun et al., U.S. Pat. No. 5,667,635 Win et al., U.S. Pat. No. 6,043,317 to Mumick et al., WO2007/110497 to Noelle, US2011/0290437 to Vogel et al., US2015/118466 Zwick et al., and so forth.

In certain embodiments, the ultra-low density tissue web described herein may comprise an outer layer or ply in the multi-ply laminate. In alternate embodiments, the multilayer tissue product may comprise 3 or more layers. In certain such embodiments and in relation to a multi-ply web having 3 or more plies, the ultra-low density tissue web described herein may comprise an inner or central ply and wherein first and second outer plies can comprise wet-laid paper tissue webs or nonwoven webs described herein above. Further, in such embodiments the first and second outer plies may be the same or different materials.

The wiping products can be provided in a stack and incorporated or oriented in a container as desired. Further, the stack of sheets can be folded as desired in order to improve efficiency of use and/or dispensing. The stack(s) of the tissue products are desirably arranged to facilitate removal or dispensing, and in certain embodiments, can be arranged to facilitate metered dispensing. The sheets may be inter-folded in various know overlapping configurations such as, for example, V-folds, Z-folds, W-folds, quarter-folds and so forth. Equipment and processes for forming dispensable stacks of wipes are known in the art; examples of which include, but are not limited to, those described in U.S. Pat. No. 3,401,927 to Frick et al.; U.S. Pat. No. 4,502,675 to Clark et al.; U.S. Pat. No. 5,310,398 to Onekama, U.S. Pat. No. 6,612,462 to Sosalla et al., and so forth. With respect to product formats utilizing a continuous length of sheet material, such as in certain rolled formats, the individually separable wet wipes desirably have perforated or over-bonded lines of weakness which allow separation into smaller individual sheets of a desired shape and size. The particular stack height and sheet count can vary with the intended format and use. However, in certain embodiments, the stack may include between 3 and 250 individual tissue products, in further embodiments may include between about 10 and 150 tissue products and in still further embodiments may include between about 10 and 90 tissue products.

The stack of tissue products may be housed within a container adapted for the maintenance and/or dispensing of wiping products. Numerous such containers, e.g. packages and/or dispensers, are known in the art and suitable for use herewith. In one aspect, the container includes a plurality of walls defining an interior space. In one aspect, the container may comprise a flexible pack formed by thin polymeric film and optionally further having a resealable or reclosable dispensing opening for accessing the tissue products contained therein. Examples of flexible packaging dispensers include, but are not limited to, those described in U.S. Pat. No. 4,863,064 to Dailey, U.S. Pat. No. 5,524,759 Herzberg et al., U.S. Pat. No. 6,012,572 Heathcock et al., U.S. Pat. No. 7,527,152 to House et al., WO96/37138 Bauer et al., US2010/155284 Foley et al. and so forth. In addition, substantially rigid dispensers suitable for dispensing the paper tissue products of the present invention include, but are not limited to, those described in U.S. Pat. No. 3,369,700 Nelson et al., U.S. Pat. No. 3,369,699 Enloe et al., U.S. Pat. No. 5,785,179 Buczwinski et al., U.S. Pat. No. 7,028,840 Huang et al., U.S. Pat. No. 7,543,423 Long et al., US2005/211718 Decker et al., US2007/0235466 Fulscher et al., and so forth. In a particular embodiment, such as seen in reference to FIG. 1, a stack 22 of individual tissue products 20 may be positioned within a container or dispenser 24. The tissue stack 22 is located within the walls 24 of the dispenser 23 and may comprise the substantial majority of the interior space of the dispenser 23. The dispenser 23 can have at least one side panel, such as a top side panel 26, having a dispensing opening 28 through which the individual tissue sheets 20 can be removed. Commonly, the dispensing opening 28 will have a tab or cover (not shown) that is positioned over the dispensing opening but which is designed to be removed by the ultimate user at the time of use. To facilitate one at a time or metered dispensing, the dispensing opening 28 can have a flexible membrane or film 27 partially occluding the dispensing opening and designed to provide a frictional force on the tissue sheet 20 being removed and thereby facilitate proper separation of the individual tissue sheet 20 from the stack 22.

Personal Care Absorbent Articles

Absorbent personal care articles generally include a liquid permeable topsheet, which faces the wearer, and a liquid-impermeable backsheet or outer cover. Disposed between the topsheet and outer cover is an absorbent core. In this regard, the topsheet and outer cover are often joined and/or sealed to encase the absorbent core. Although certain aspects of the present invention are described in the context of a particular personal care absorbent article, it will be readily appreciated that similar uses in other types of personal care absorbent articles and/or further combinations or alterations of the specific configurations discussed below may be made by one skilled in the art without departing from the spirit and scope of the present invention.

Figure 2:
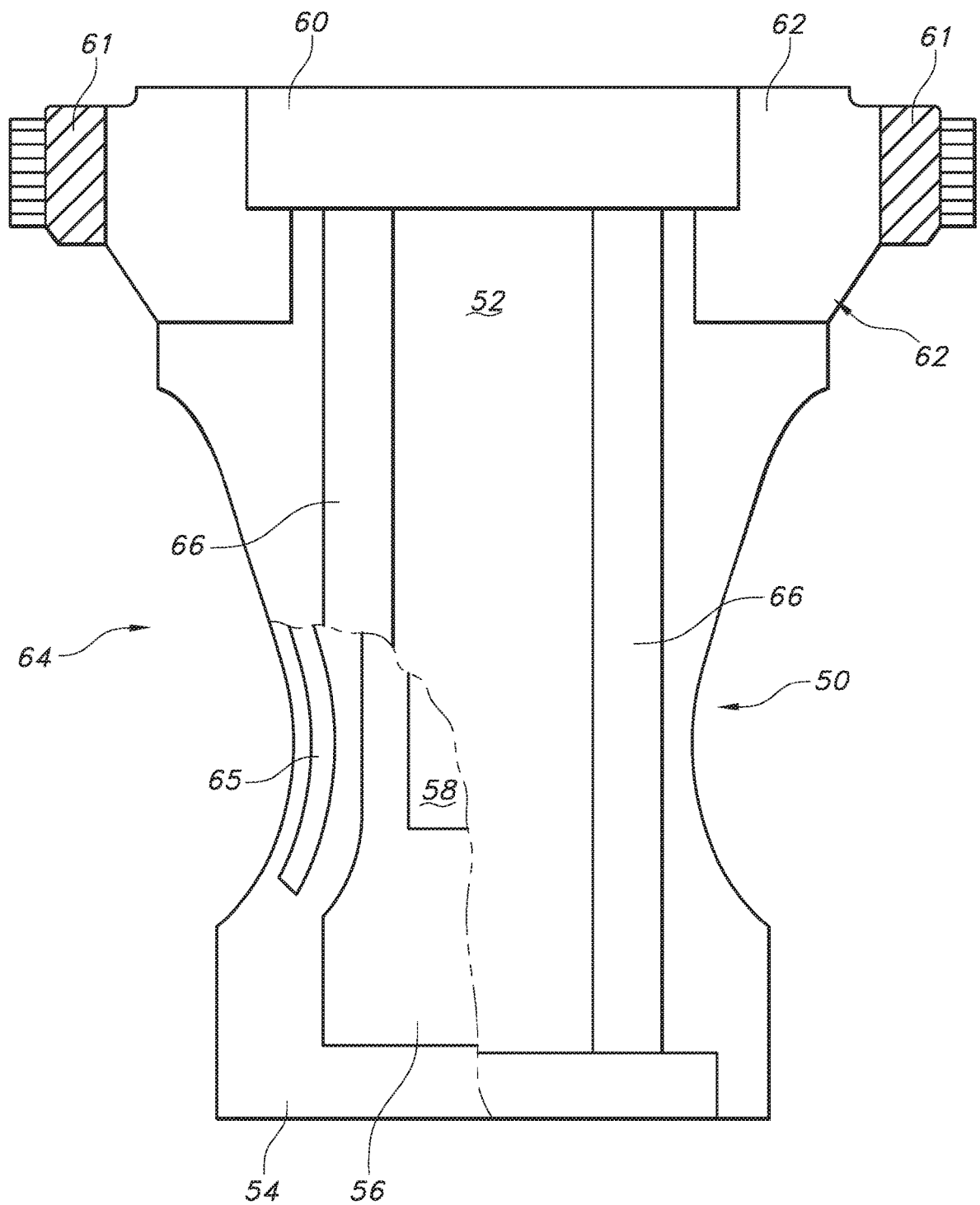
FIG. 2 is a top, plan view of an absorbent personal care article including an absorbent material of the present invention.

In a particular embodiment, and in reference to FIG. 2, a diaper 50 can comprise a liquid-impervious outer cover 54, a liquid permeable topsheet 52 positioned in facing relation to the outer cover 54, and an absorbent core 56 between the outer cover 54 and topsheet 52. The diaper 50 may be of various shapes such as, for example, an overall rectangular shape, T-shape, hourglass shape and so forth. The topsheet 52 is generally coextensive with the outer cover 54 but may optionally cover an area that is larger or smaller than the area of the outer cover 54, as desired. While not shown, it is to be understood that portions of the diaper, such as a marginal section of the outer cover, may extend past and around the terminal edges of the product and form a portion of the body-facing layer. The diaper 50 also has end margins 62 adapted to fit about the waist of the wearer and a central region 64 designed to extend about the groin region as well as provide leg openings in combination with end margins 62. Fastening members 61 are commonly located adjacent the end margins 62 for securing the diaper about the wearer.

The topsheet or body-side liner 52, as representatively illustrated in FIG. 2, desirably presents a body facing surface which is compliant, soft to the touch, and non-irritating to the wearer's skin. The topsheet 52 is desirably employed to help isolate the wearer's skin from liquids held in the absorbent core 56. Topsheets are well known in the art and may be manufactured from a wide variety of materials, such as porous foams, reticulated foams, apertured plastic films, natural fibers (wool, cotton fibers, etc.), synthetic fibers (polyester, polypropylene, polyethylene, etc.), combinations of natural and synthetic fibers, and so forth. Topsheets can comprise a single layer or a multiple layers including a combination of one or more different materials. Nonwoven fabrics, and laminates thereof, are commonly utilized to form topsheets. Suitable topsheet materials include, but not limited to, those described in U.S. Pat. No. 5,382,400 to Pike et al.; U.S. Pat. No. 5,415,640 to Kirby et al.; U.S. Pat. No. 5,527,300 to Sauer; U.S. Pat. No. 5,994,615 to Dodge et al.; U.S. Pat. No. 6,383,960 to Everett et al.; U.S. Pat. No. 6,410,823 to Daley et al.; US2014/0121623 to Biggs et al. and so forth.

The backsheet or outer cover 54 comprises a liquid-impervious material. Desirably, the outer cover comprises a material that prevents the passage of water but allows air and water-vapor to pass there through. The outer cover can comprise a single layer of material or multiple layers including one or more layers of different materials. In a particular embodiment, the outer cover can comprise a film fixedly attached or bonded to one or more nonwoven webs. The particular structure and composition of the outer cover may be selected from various combinations of films and/or fabrics. In this regard, the outer most layers are generally selected for providing the desired strength, abrasion resistance, tactile properties and/or aesthetics. As an example, nonwoven fabrics are commonly employed as the outermost layer of the outer cover. Suitable outer covers include, but are not limited to, those described in U.S. Pat. No. 4,041,203 to Brock et al.; U.S. Pat. No. 6,075,179 et al. to McCormack et al.; U.S. Pat. No. 6,111,163 to McCormack s et al.; US2015/099086 to Cho et al. and so forth.

Between the liquid-impervious outer cover 54 and the liquid pervious topsheet 52 is positioned an absorbent core 56. The absorbent core may itself comprise a multiple layers having similar or different absorbent properties. In this regard, the absorbent core often includes one or more absorbent materials including, but not limited to, superabsorbent particles, wood pulp fibers, synthetic wood pulp fibers, synthetic fibers and combinations thereof. The absorbent core may have any of a number of shapes and the size of the absorbent core and selection of materials therein will vary with the desired loading capacity, the intended use of the absorbent article and other factors known to those skilled in the art. Examples of various absorbent core structures and/or additional absorbent materials that may be used in conjunction with the present invention include, but are not limited to, those described in U.S. Pat. No. 4,699,823 to Kellenberger et al.; U.S. Pat. No. 5,458,592 to Abuto et al; U.S. Pat. No. 5,601,542 to Melius et al.; U.S. Pat. No. 6,129,720 to Blenke et al.; U.S. Pat. No. 6,383,960 to Everett et al.; U.S. Pat. No. 7,938,813 to Elliker et al.; US2002/0183703 Dodge et al. and so forth. In one aspect, the absorbent core may include one or more layers, wherein at least one layer comprises the ultra-low density cellulosic tissue sheet described herein. In certain embodiments, the absorbent core may include a stack of ultra-low density cellulosic tissue sheets.

In addition, it is also common for the personal care absorbent article to employ a liquid distribution layer or "wicking" layer 58 above the absorbent core 56 in order to increase the span and/or regulate the speed with which the liquid coming into the absorbent article reaches the absorbent core. However, in other embodiments, the liquid transfer layer may alternatively and/or additionally be placed beneath the absorbent core (not shown). Such materials can comprise one or more nonwoven webs including for example, but not limited to multi-functional air-laid materials, apertured film/nonwoven laminates, high-loft nonwoven fabrics and so forth. Examples of various liquid distribution layers include, but are not limited to, those described in U.S. Pat. No. 5,364,382 to Latimer et al.; U.S. Pat. No. 6,437,214 to Bolwerk et al.; U.S. Pat. No. 6,534,149 Mace et al.; U.S. Pat. No. 6,617,490 Lindsay et al and so forth. In certain embodiments, the absorbent personal care article may include a liquid distribution layer comprising an ultra-low density cellulosic material described herein.

The personal care articles can, optionally, contain one or more additional elements or components. In this regard, numerous additional features and various constructions are known in the art. As but a few examples and in reference to FIG. 2, the diaper can further include elastic leg cuffs 65, an elastic waistband 60, fluid control flaps 66, and so forth. One skilled in the art will appreciate the application and use of the ultra-low density webs of the present invention in like manners for other absorbent personal care articles including, for example, adult incontinence garments, incontinence pads/liners, sanitary napkins, party-liners, sweat pads, bandages, and so forth. In addition, other absorbent articles that may include one or more layers of the ultra-low density webs of the present invention including, but are not limited to, baby bibs and changing pads, bed pads, food tray liners, and so forth.

The cellulosic tissue webs and products can, optionally, include one or more additional elements or components as are known in the art. Thus, while the invention has been described in detail with respect to specific embodiments and/or examples thereof, it will be apparent to those skilled in the art that various alterations, modifications and other changes may be made to the invention without departing from the spirit and scope of the same. It is therefore intended that the claims cover or encompass all such modifications, alterations and/or changes.

Definitions and Test Methods

In reference to the Figures and throughout the specification and claims, discussion of the articles and/or individual components thereof is with the following understanding:

The terms "comprising" or "including" or "having" are inclusive or open-ended and do not exclude additional unrecited elements, compositional components, or method steps. Accordingly, the terms "comprising" or "including" or "having" also encompass the more restrictive terms "consisting essentially of" and "consisting of".

As used herein, the term "basis weight" generally refers to the bone dry weight per unit area of a tissue and is generally expressed as grams per square meter (gsm). Basis weight is measured using TAPPI test method T-220 sp-10.

As used herein, the term "nonwoven web" means a web having a structure of individual fibers or threads which are interlaid, but not in an identifiable manner as in a knitted web.

The term "personal care absorbent article" refers herein to an article intended and/or adapted to be placed against or in proximity to the body (i.e., contiguous with the body) of the wearer to absorb and contain various liquid, solid, and semi-solid exudates discharged from the body. Examples include, but are not limited to, diapers, diaper pants, training pants, youth pants, swim pants, feminine hygiene products, including, but not limited to, menstrual pads or pants, incontinence products, medical garments, surgical pads and bandages, and so forth.

The term "ply" refers to a discrete layer within a multi-layered product wherein individual plies may be arranged in juxtaposition to each other.

The term "plied" or "bonded" or "coupled" refers herein to the joining, adhering, connecting, attaching, or the like, of two elements. Two elements will be considered plied, bonded or coupled together when they are joined, adhered, connected, attached, or the like, directly to one another or indirectly to one another, such as when each is directly bonded to intermediate elements. The plying, bonding or coupling of one element to another can occur via continuous or intermittent bonds.

As used herein, unless expressly indicated otherwise, when used in relation to material compositions the terms "percent", "percent", "weight percent" or "percent by weight" each refer to the quantity by weight of a component as a percentage of the total.

As used herein, the term "stack" is used broadly to include any collection of sheets wherein there is a plurality of individual sheets having surface-to-surface interfaces; this not only includes a vertically stacked collection of individual sheets, but also includes a horizontally stacked collection of individual sheets as well as a rolled or folded collection of continuous sheet material separated by lines of weakness (e.g. perforations).

As used herein "caliper" or "thickness" of a sheet is determined by using a micrometer having an acrylic platen with a pressure foot area of 45.6 cm$^2$ (3 inch diameter), providing a load of 0.345 kPa (0.5 psi), and the reading is taken after a dwell time of 3 seconds. A sample is cut having a size of 90×102 mm (3.5×4 inches) is used for the measurement.

As used herein "Gelbo Lint Value" is determined in accordance with INDA Standard Procedure 160.1.RO (12) using the counting method C. This test determines the relative number of particles released from a fabric when it is subjected to a flexing and twisting movement.

As used herein "tensile" strength, "Dry Tensile Strength" or "Wet Tensile Strength", is the peak load value, i.e. the maximum force produced by a specimen when it is pulled to rupture. Samples for tensile strength testing are prepared by cutting a 76 mm wide strip of the sheet to be tested and then conditioning the specimen by hanging in an oven at 105 C for six minutes. The instrument used for measuring tensile strengths is an Instron Tensile Tester and the data acquisition software is MTS TestWorks™ for Windows Ver. 4 (MTS Systems Corp., Research Triangle Park, NC). The load cell is selected from either a 50 Newton or 102 Newton maximum, depending on the strength of the sample being tested, such that the majority of peak load values fall between 10 and 90 percent of the load cell's full scale value. The gauge length between jaws is 100 mm. The jaws are operated using pneumatic-action and are rubber coated. The grip face width is 76, and the approximate height of a jaw is 13 mm. The crosshead speed is 254 mm/minute, and the break sensitivity is set at 65 percent, slack compensation is set at 25 g. The sample is placed in the jaws of the instrument, centered both vertically and horizontally. The test is then started and ends when the specimen breaks. The peak load is recorded as either the "MD tensile strength" or the "CD tensile strength" of the specimen depending on the sample being tested. Six (6) representative specimens are tested for each product, and the arithmetic average of all individual specimen tests is either the MD or CD tensile strength for the product. For purposes of the present invention, the tensile refers to the higher value of the CD or MD as applicable. Wet tensile strength measurements are measured in the same manner, with the exception that the center portion of the previously conditioned sample strip has been saturated with distilled water immediately prior to loading the specimen into the tensile test equipment. Sample wetting is performed by first laying a single test strip onto a piece of blotter paper (Fiber Mark, Reliance Basis 120). A pad is then used to wet the sample strip prior to testing. The pad is a green, Scotch-Brite brand (3M) general purpose commercial scrubbing pad. To prepare the pad for testing, a full-size pad is cut approximately 2.5 inches long by 4 inches wide. A piece of masking tape is wrapped around one of the 4-inch long edges. The taped side then becomes the "top" edge of the wetting pad. To wet a tensile strip, the tester holds the top edge of the pad and dips the bottom edge in approximately 0.25 inches of distilled water located in a wetting pan. After the end of the pad has been saturated with water, the pad is then taken from the wetting pan and the excess water is removed from the pad by lightly tapping the wet edge three times across a wire mesh screen. The wet edge of the pad is then gently placed across the sample, parallel to the width of the sample, in the approximate center of the sample strip. The pad is held in place for approximately one second and then removed and placed back into the wetting pan. The wet sample is then immediately inserted into the tensile grips so the wetted area is approximately centered between the upper and lower grips. The test strip should be centered both horizontally and vertically between the grips. (It should be noted that if any of the wetted portion comes into contact with the grip faces, the specimen must be discarded and the jaws dried off before resuming testing.) The tensile test is then performed and the peak load recorded to obtain the wet tensile strength.

EXAMPLES

The below examples were made according to the following process. A total of 2000 grams of a slurry was added into a disintegrator's cup for fiberizing wood pulp fiber. The slurry was formed to having a fiber consistency of about 2%. 40 grams of dry commercial densified wood pulp sheet and, where applicable additional fibers, were weighed according to fiber mixture weight ratio and placed into the British standard disintegrator's cup. 1960 grams of distilled water was added into the cup and the fiber mixture was soaked for 5 minutes. The cup was then mounted onto the disintegrator and ran for 15,000 revolutions to sufficiently fiberize the wood pulp fiber. After this, 500 grams of the slurry was weighed in a separate container having a dimension of 150 mm in diameter and 170 mm in height and 6.5 grams of 10% sodium dodecyl sulfate solution was added into the container. The surfactant concentration in the slurry was about 0.13 weight percent. The slurry was mixed by a high speed rotary mixer at a speed of 4000 rpm for several minutes until the vertex inside the container disappeared.

The foam formed fiber slurry was then shaped into a sheet by two different ways. Method 1 was to pour entire foamed slurry into a lab hand sheet former with an area dimension of 10 inches by 10 inches. Method 2 was to control thickness of the wet foam sheet by push it through a gap with the gap height controlled through the use of different diameter metal rods.

The foam sheets were dried in an oven at 90° C. for about 2 to 3 hours. Optionally, the dried base sheets were subsequently heat cured at a temperature suitable to activate binder fiber to achieve its thermo-bonding.

Example 1

Foam formed base sheet comprising only wood pulp fiber; the wood pulp fiber consisted of a mixture of northern softwood kraft fiber (LL-19) and *Eucalyptus* fiber.

Example 2

Foam formed base sheet comprising both wood pulp fiber and a binder fiber. The wood pulp fiber consisted of a mixture of northern softwood kraft fiber (LL-19) and *Eucalyptus* fiber. The binder fiber comprised Trevira T255-6 polyethylene/PET sheath/core staple fiber with a 6 mm fiber length and 2.2 dtex. After drying, the web was further heated at 130 C for one hour cured in order to activate the binder fiber.

The low density webs of the examples were tested and the properties are reported in the table below.

TABLE 1

A Summary of Different Base Sheets with Compositions & Certain Basic Properties

| | | Foam Forming Slurry Composition | | | | | Properties | |
|---|---|---|---|---|---|---|---|---|
| | | Pulp | | Binder | | | | |
| Sample No. | Base Sheet Description | Euc (g) | LL-19 (g) | Fiber T255-6 (g) | Surfactant SDS (g) | Water (g) | Basis Weight (g/m²) | Density (g/cm³) |
| 1 | Foam Formed | 10.5 | 4.5 | — | 0.65 | 485 | 135 | 0.016 |
| 2 | Foam Formed | 10.5 | 4.5 | 1.5 | 0.65 | 485 | 139 | 0.0157 |

TABLE 2

A Summary of Tensile Testing and Lint Content Testing Results

| | Tensile Testing Results | | Average Number of Linting Particles Shaking Out from the Substrates | | | Lint |
|---|---|---|---|---|---|---|
| Code ID | Dry (g·force) | Wet (g·force) | >5.0 µm | >10.0 µm | >25.0 µm | Content (Sum) |
| 1 | 116 | 22 | 1.6 | 0.8 | 0.4 | 2.8 |
| 2 | 920 | 255 | 0.8 | 0.7 | 0.1 | 1.6 |

What is claimed is:

1. A tissue paper product comprising:
    a first ply having a highly porous, open-celled structure comprising cellulosic fibers, a water insoluble binder and a foaming surfactant, wherein the water insoluble binder comprises thermoplastic binder fibers, and wherein the cellulosic fiber comprises greater than 50% by weight of the first ply;
    said cellulosic fibers of said first ply are bonded to one another by hydrogen bonding; and
    wherein said first ply has a density less than about 0.04 g/cc, Gelbo Lint Value less than 5 and a wet tensile strength of at least 10 g-f.

2. The tissue paper product of claim 1 wherein said first ply has a substantially planar, sheet-like structure having a thickness of between about 0.5 and about 5 mm.

3. The tissue paper product of claim 1 wherein said thermoplastic binder fibers comprise less than about 10% by weight of said first ply.

4. The tissue paper product of claim 1 further comprising a wet strength resin adhered to said cellulosic fibers and selected from the group consisting of cationic oligomeric or polymeric resins.

5. The tissue paper product of claim 2 wherein the density of said first ply is between about 0.02 g/cc and about 0.005 g/cc.

6. The tissue paper product of claim 1 wherein said foaming surfactant is selected from cationic and anionic surfactants and is present in said first ply in an amount between about 0.1 and about 5%.

7. The tissue paper product of claim 1 further comprising a second ply comprising a wet-laid tissue including at least 95% wood pulp fibers by weight of the second ply and having a density between about 0.5 and 0.04 g/cc, and further wherein said first and second plies are attached to one another.

8. The tissue paper product of claim 7 wherein the first and second plies are pattern embossed.

9. The tissue paper product of claim 7 further comprising a third ply comprising a wet-laid tissue including at least 95% wood pulp fibers by weight of the third ply and having a density between about 0.5 and 0.04 g/cc, and wherein said first ply is positioned between said second and third plies and said first, second and third plies are attached to one another.

10. A packaged wiping product comprising:
a container defining an interior space;
a stack of between 3 and 150 individual wiping sheets, said stack located within said interior space;
said wiping sheets comprising the tissue paper product of claim 1.

11. The packaged wiping product of claim 10 wherein said container has a reclosable dispensing opening.

12. The packaged wiping product of claim 10 wherein said container has a dispensing opening and a flexible film partially occluding said dispensing opening.

13. The packaged wiping product of claim 11 wherein the density of said first ply is between about 0.02 g/cc and about 0.005 g/cc.

14. The packaged wiping product of claim 13 further comprising a second ply comprising a wet-laid tissue including at least 95% wood pulp fibers by weight of the second play and having a density between about 0.5 and 0.04 g/cc, and further wherein said first and second plies are attached to one another.

15. The packaged wiping product of claim 14 wherein said stack comprises either (i) a roll of individual wiping sheets separated by lines of perforation or (ii) superposed, inter-folded wiping sheets.

16. A personal care absorbent article comprising:
a liquid pervious body-side liner;
a liquid impervious outer cover;
an absorbent core, said absorbent core is located between and said body-side liner and said outer cover; and
wherein the absorbent core includes the tissue paper product of claim 1.

17. The absorbent personal care article of claim 16 wherein the first ply of said tissue paper product has a sheet-like structure having a thickness of between about 5 mm and about 40 mm and a density of between about 0.02 g/cc and about 0.005 g/cc.

18. The absorbent personal care article of claim 17 wherein the absorbent core further includes superabsorbent particles.

19. A personal care absorbent article comprising:
a liquid pervious body-side liner;
a liquid impervious outer cover;
an absorbent core, said absorbent core is located between and said body-side liner and said outer cover; and
a liquid transfer layer superposed with said absorbent core and located between and said body-side liner and said outer cover; and
wherein the liquid transfer layer includes the tissue paper product of claim 1.

20. The absorbent personal care article of claim 19 wherein the first play of said tissue paper has a sheet-like structure having a thickness of between about 0.5 and about 5 mm and a density between about 0.02 g/cc and about 0.005 g/cc.

21. The tissue paper product of claim 1, wherein the Gelbo Lint Value is less than 2.8.

22. The tissue paper product of claim 1, wherein the tissue paper product is free from a polymeric foamable binder material.

* * * * *